Figure 1:
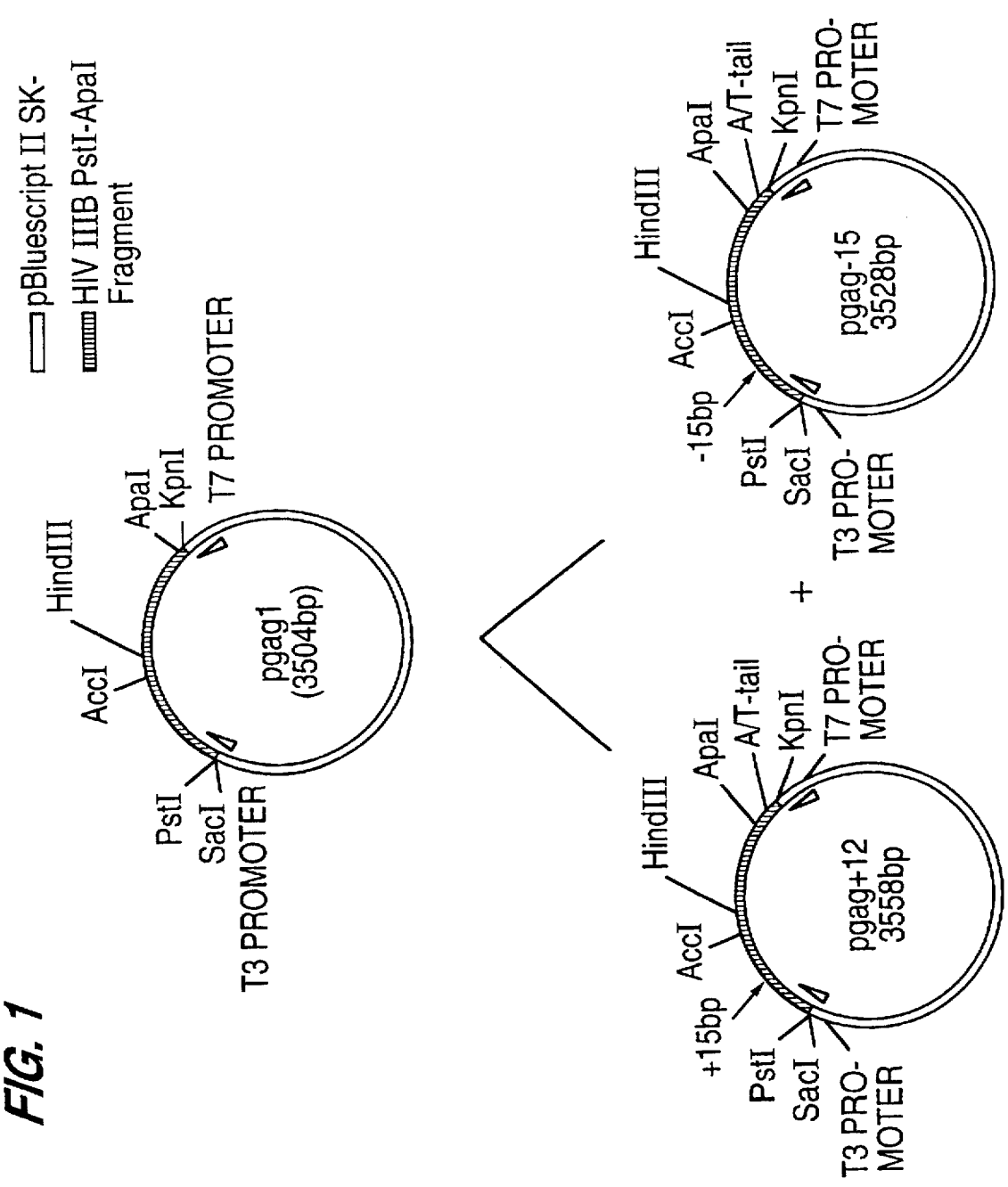
Figure 2A:
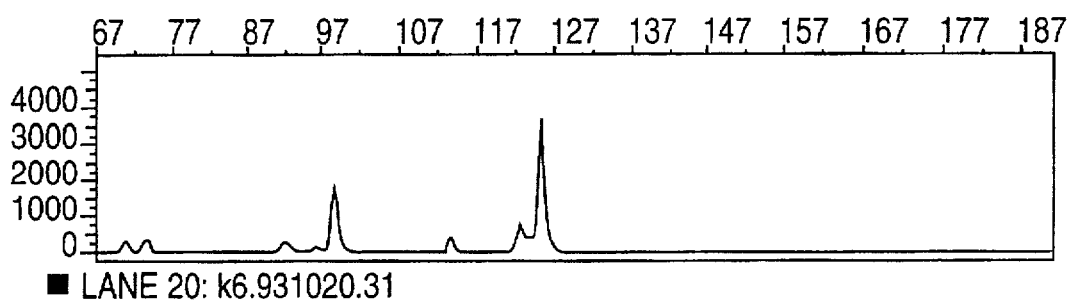
Figure 2B:
Figure 2C:
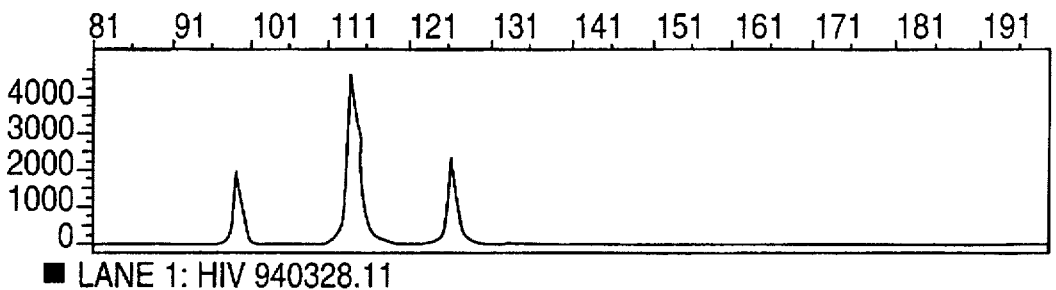
Figure 2D:
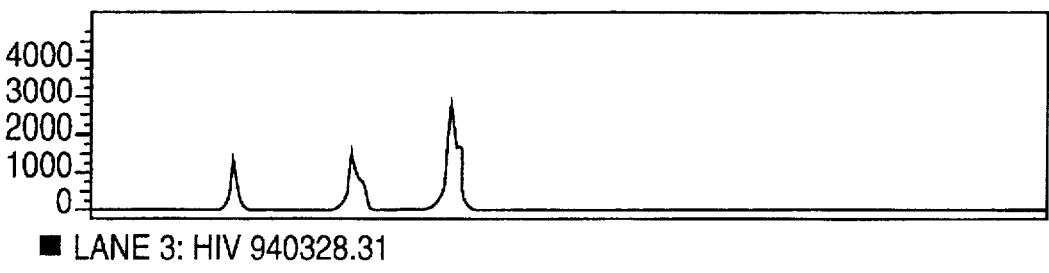
Figure 2E:
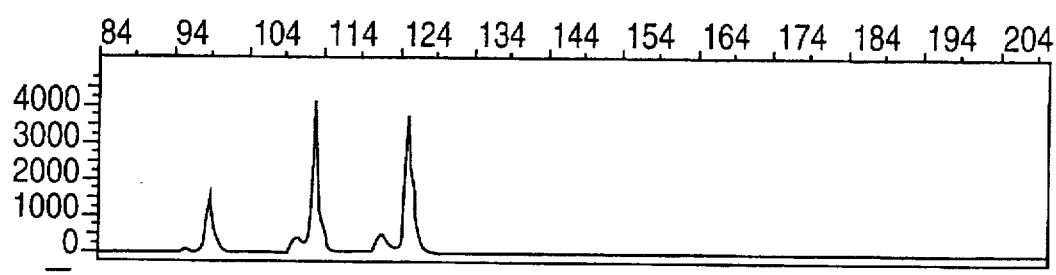
Figure 2F:
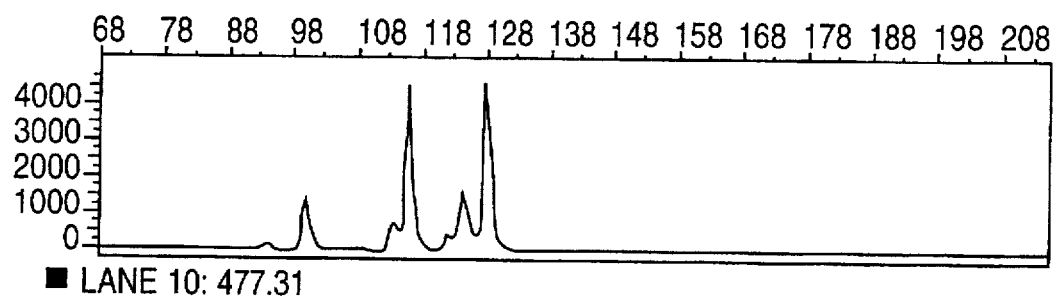

United States Patent [19]
Falkner et al.

[11] Patent Number: 5,789,153
[45] Date of Patent: Aug. 4, 1998

[54] METHOD OF QUANTITATING NUCLEIC ACID

[75] Inventors: Falko-Guenter Falkner; Thomas Haemmerle, both of Orth/Donau; Michele Himmelspach, Vienna; Johann Kohl, Vienna; Friedrich Dorner, Vienna, all of Austria

[73] Assignee: Immuno Aktiengesellschaft, Vienna, Austria

[21] Appl. No.: 533,820

[22] Filed: Sep. 26, 1995

[30] Foreign Application Priority Data

Sep. 26, 1994 [AT] Austria .................. 1831/94
Dec. 2, 1994 [AT] Austria .................. 2245/94

[51] Int. Cl.$^6$ .............. C12P 19/34; C07H 21/04; C07H 21/02; C12N 15/09
[52] U.S. Cl. .............. 435/5; 435/91.2; 435/320.1; 536/24.3; 536/22.1; 536/25.32
[58] Field of Search .............. 435/91.2, 320.1, 435/5; 536/24.3, 22.1, 25.32

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,491,063 | 2/1996 | Fisher et al. | 435/6 |
| 5,523,204 | 6/1996 | Singer et al. | 435/5 |

FOREIGN PATENT DOCUMENTS

| | | | |
|---|---|---|---|
| 0 551 712 A1 | 4/1992 | European Pat. Off. | C12Q 1/68 |
| 0521318A2 | 1/1993 | European Pat. Off. | |
| 0521318A3 | 1/1993 | European Pat. Off. | |
| 93/23573 | 11/1993 | WIPO | |
| WO 93/23573 | 11/1993 | WIPO | |
| WO 94/10342 | 5/1994 | WIPO | |
| 94/20640 | 9/1994 | WIPO | |
| WO 95/02067 | 1/1995 | WIPO | |

OTHER PUBLICATIONS

Apostolakos et al. Measurement of Gene Expression by multiplex Competitive Polymerase Chain Reaction, Analytical Biochemistry, vol. 213, pp. 277–284, 1993.

Pocher et al. A Simplified Method for Determination of Specified DNA or RNA Copy Number Using Quantitative PCR and an automatic DNA Sequencer., Bio Techniques, vol. 13(1), pp. 106–113, 1992.

Wang et al. Quantitation of mRNA by the Polymerase Chain Reaction, Proc. Natl. Acad. Sci. USA, vol. 86, pp. 9717–9721, 1989.

Van Gemen et al. Journal Of Virological Methods 49: 157–167 (1994).

Piatak et al. Biotechniques 14(1): 70–80 (1993).

Gilliland et al., "Analysis of Cytokine mRNA and DNA: Detection And Quantitation By Competitive Polymerase Chain Reaction", Proc. Natl. Acad. Sci. USA, vol. 87:2725–2729, (1990).

Wang et al., "Quantitation of mRNA By The Polymerase Chain Reaction", Proc. Natl. Acad. Sci. USA, vol. 86:9717–9721, (1989).

Porcher et al., "A Simplified Method For Determination of Specific DNA or RNA Copy Number Using Quantitative PCR and An Automatic DNA Sequencer", Biotechniques, vol. 13, No. 1, pp. 106–113, (1992).

Cohen et al., "Complete Nucleotide Sequence of Wild–Type Hepatitis A Virus: Comparison With Different Strains of Hepatitis A Virus and Other Picornaviruses", Journal of Virology, vol. 61, No.1, pp. 50–59, (1987).

Han et al., "Characterization of The Terminal Regions of Hepatitis C Viral RNA: Identification of Conserved Sequences in The 5'Untranslated Region And Poly(A) Tails At The 3'End", Proc. Natl. Acad. Sci. USA, vol. 88:1711–1715, (1991).

Fujiyama et al., "Cloning And Structural Analyses of Hepatitis B Virus DNAs, Subtype adr", Nucleic Acids Research, vol. 11, No. 13, pp. 4601–4611, (1983).

Goebel et al., "The Complete DNA Sequence of Vaccinia Virus", Virology, vol. 179:247–266, (1990).

Ratner et al., "Complete Nucleotide Sequence of The AIDS Virus, HTLV–III", Nature, vol. 313:277–283, (1985).

Saiki et al., "Primer–Directed Enzymatic Amplification of DNA With A Thermostable DNA Polymerase", Science, vol. 239:487–491, (1987).

Mullis et al., "Specific Synthesis of DNA in Vitro via A Polymerase–Catalyzed Chain Reaction", Methods In Enzymology, vol. 155:335–351.

Primary Examiner—Kenneth R. Horlick
Assistant Examiner—Joyce Tung
Attorney, Agent, or Firm—Foley & Lardner

[57] ABSTRACT

There is disclosed a method of quantitating nucleic acids in a sample by using nucleic acid amplification, wherein, prior to the amplification step, a given amount of a known nucleic acid molecule is added to the sample as internal standard, which standard nucleic acid molecule differs from the nucleic acid to be quantitated by at least one detectable characteristic; to obtain a high precision and good reproducibility, known amounts of at least two known nucleic acid molecules which differ from each other and from the nucleic acid to be quantitated in at least one detectable characteristic are added as an internal standard to the sample prior to nucleic acid amplification, the amounts of amplified sample and standard nucleic acids obtained are determined, and from the amounts obtained, the amount of the nucleic acid to be quantitated originally present in the sample is determined.

28 Claims, 10 Drawing Sheets

■ LANE 20: k6.931020.31

■ LANE 21: k6.931020.41

■ LANE 1: HIV 940328.11

■ LANE 3: HIV 940328.31

■ LANE 10: 477.31

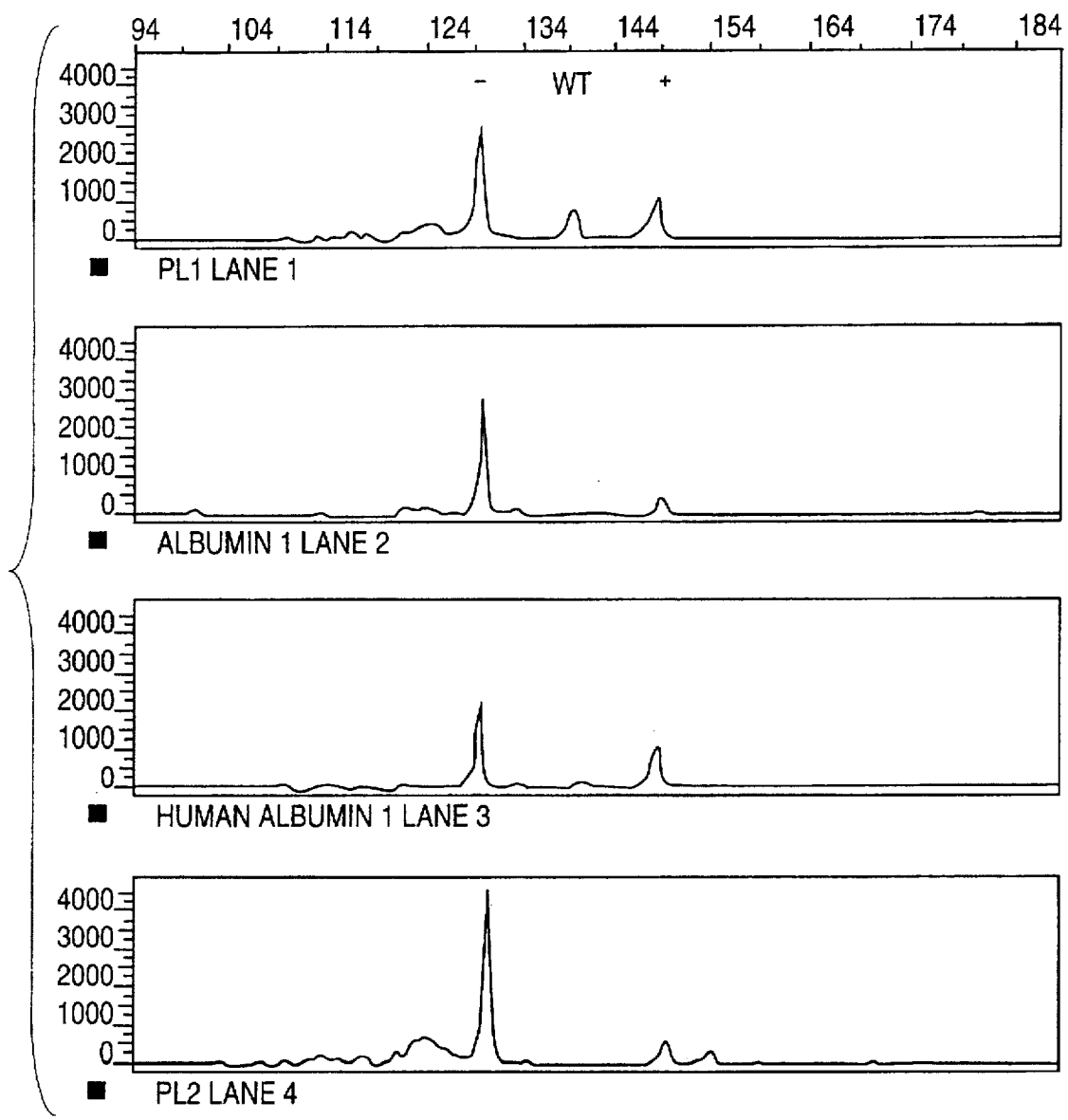
FIG. 3-A

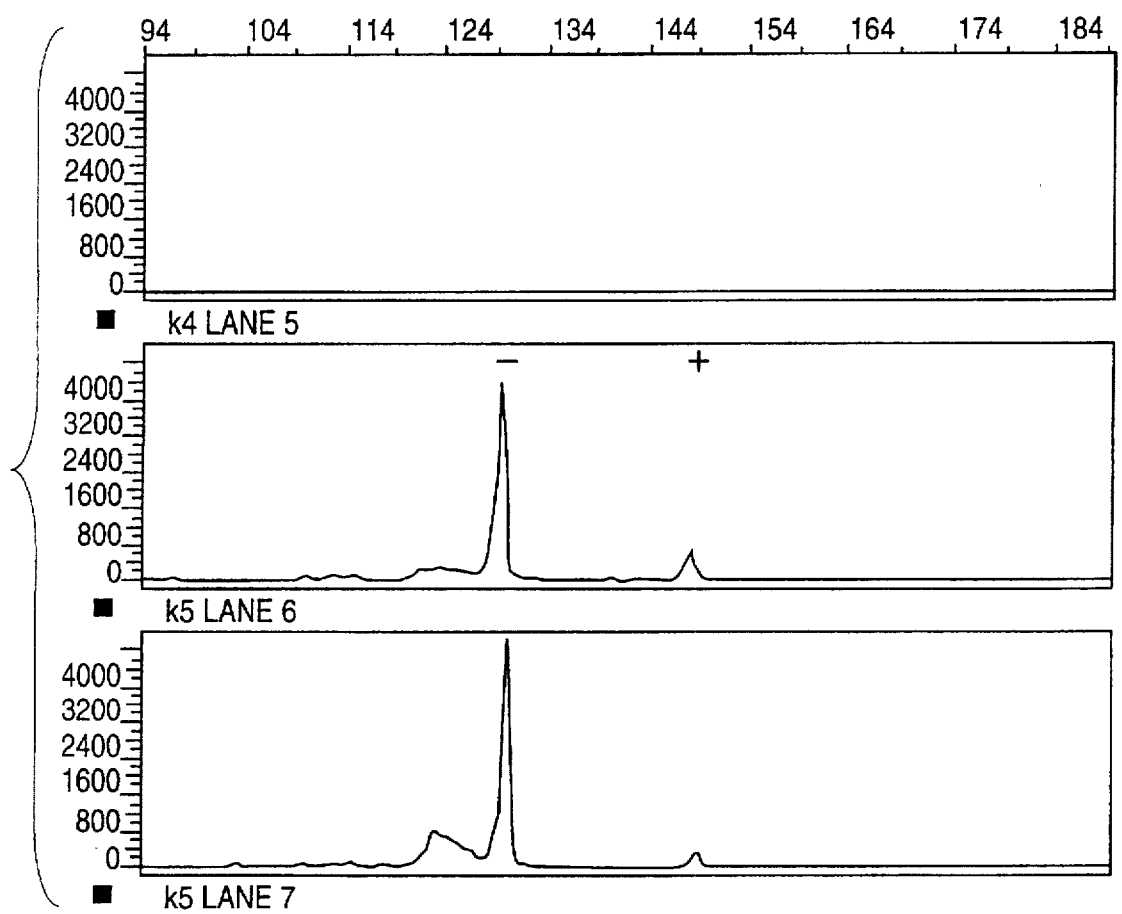
FIG. 3-B

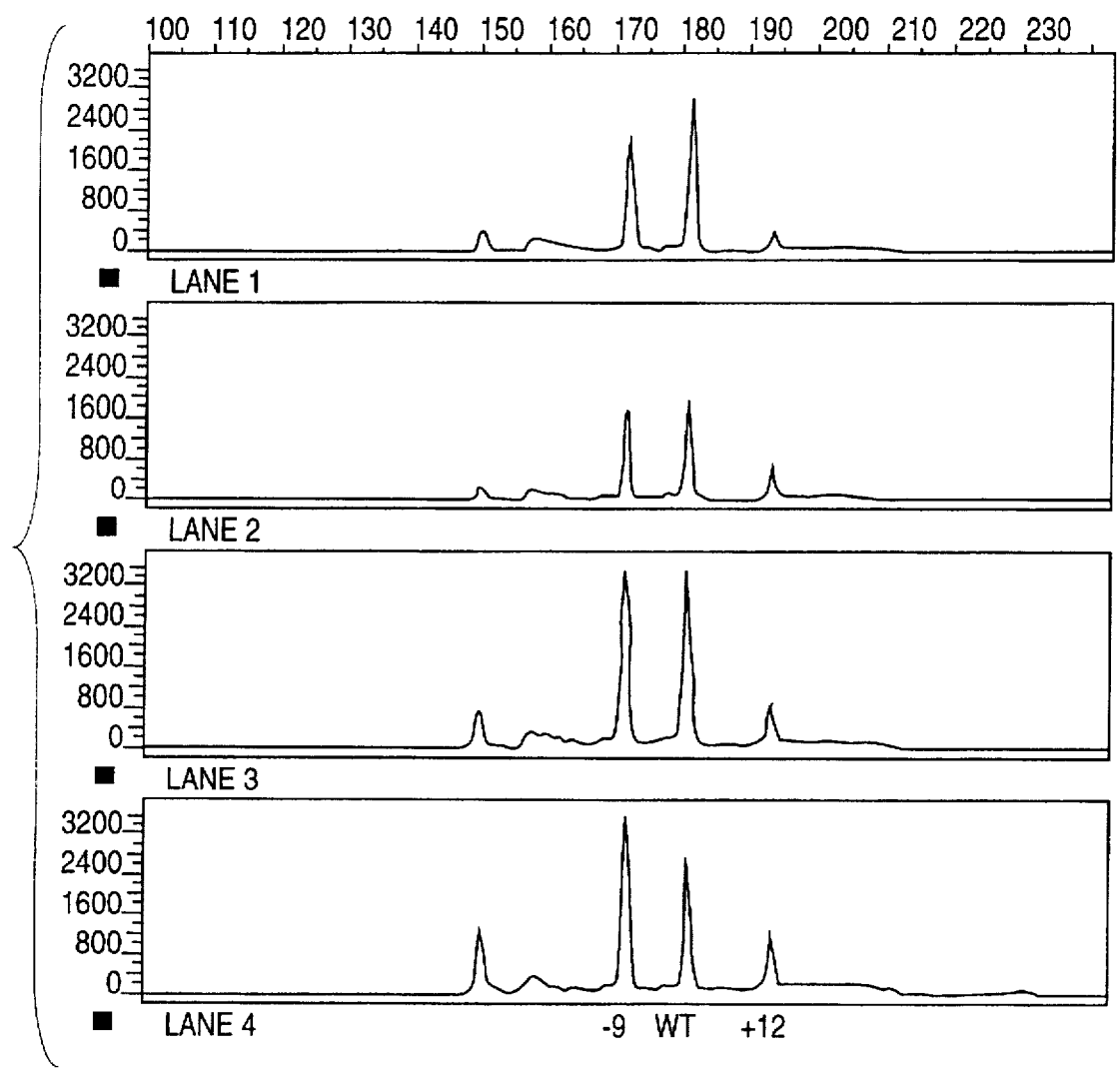
FIG. 4-A

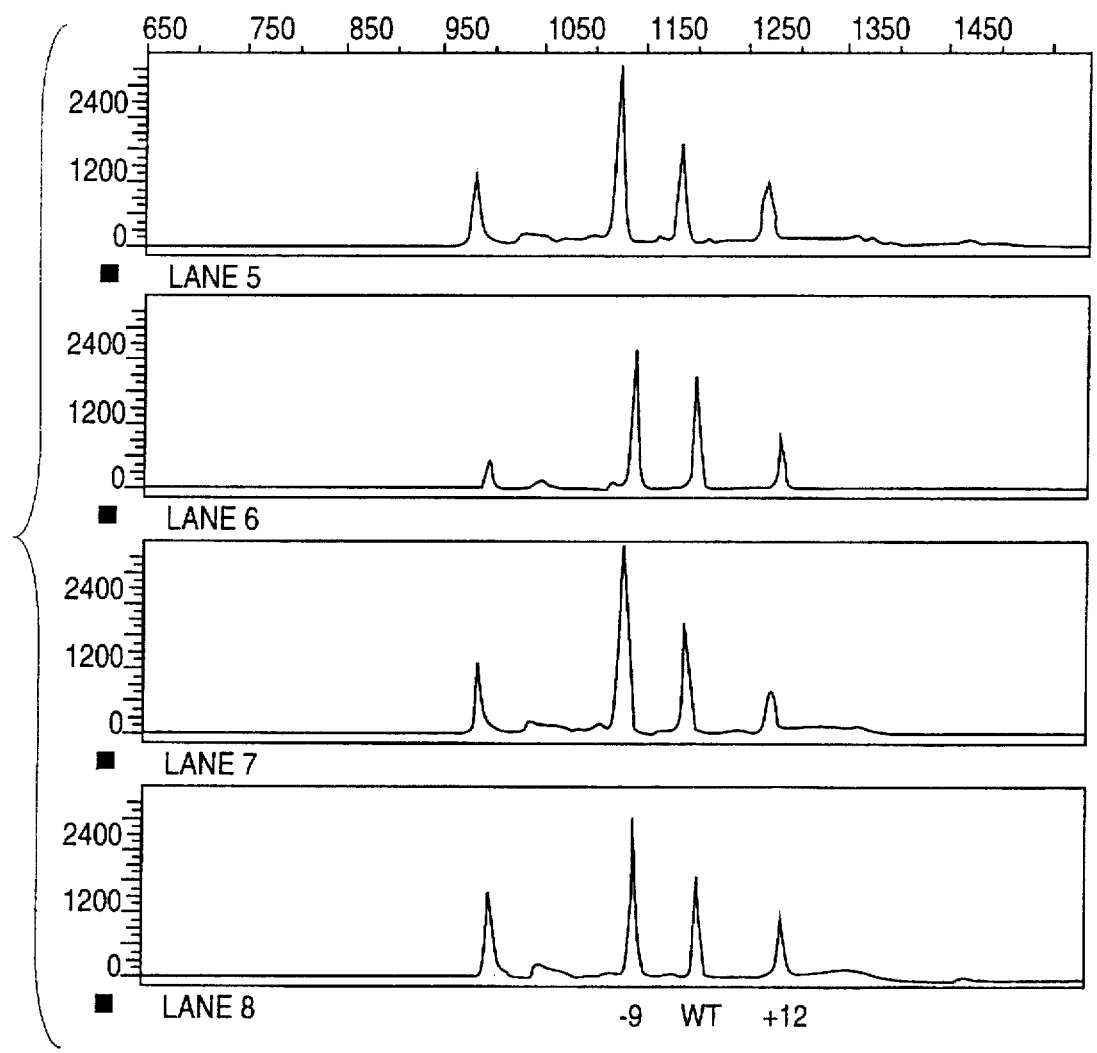
FIG. 4-B

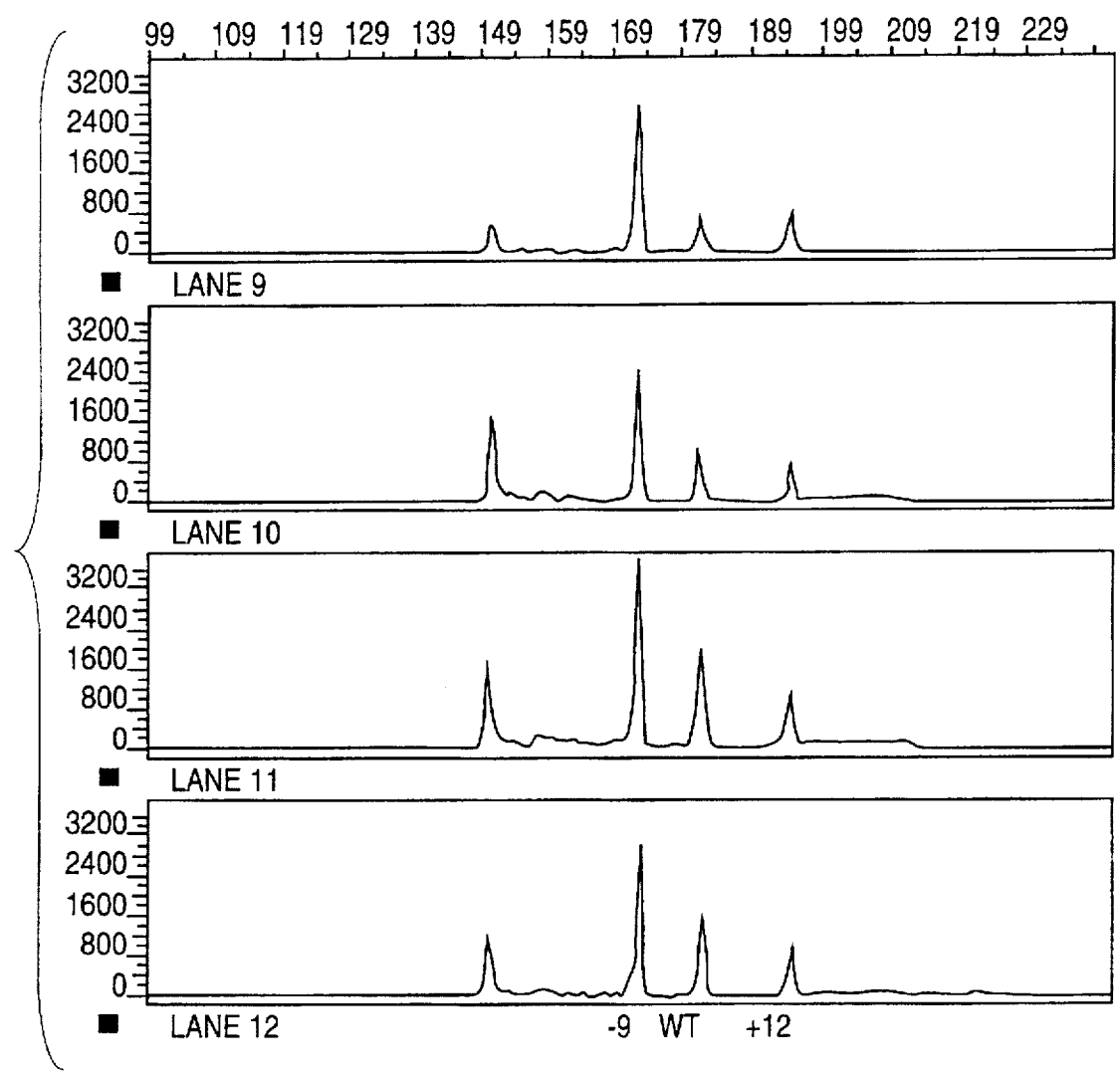
FIG. 4-C

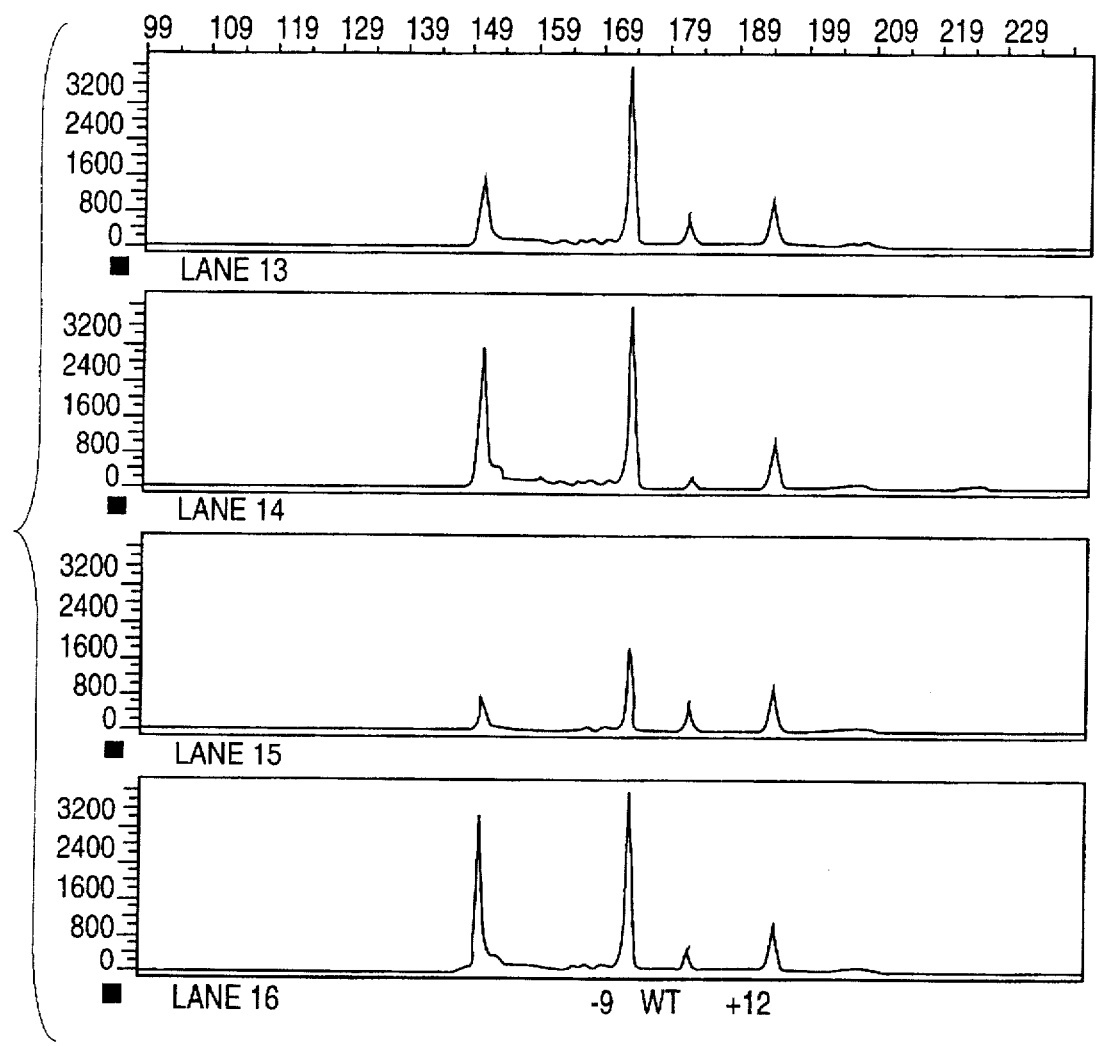
FIG. 4-D

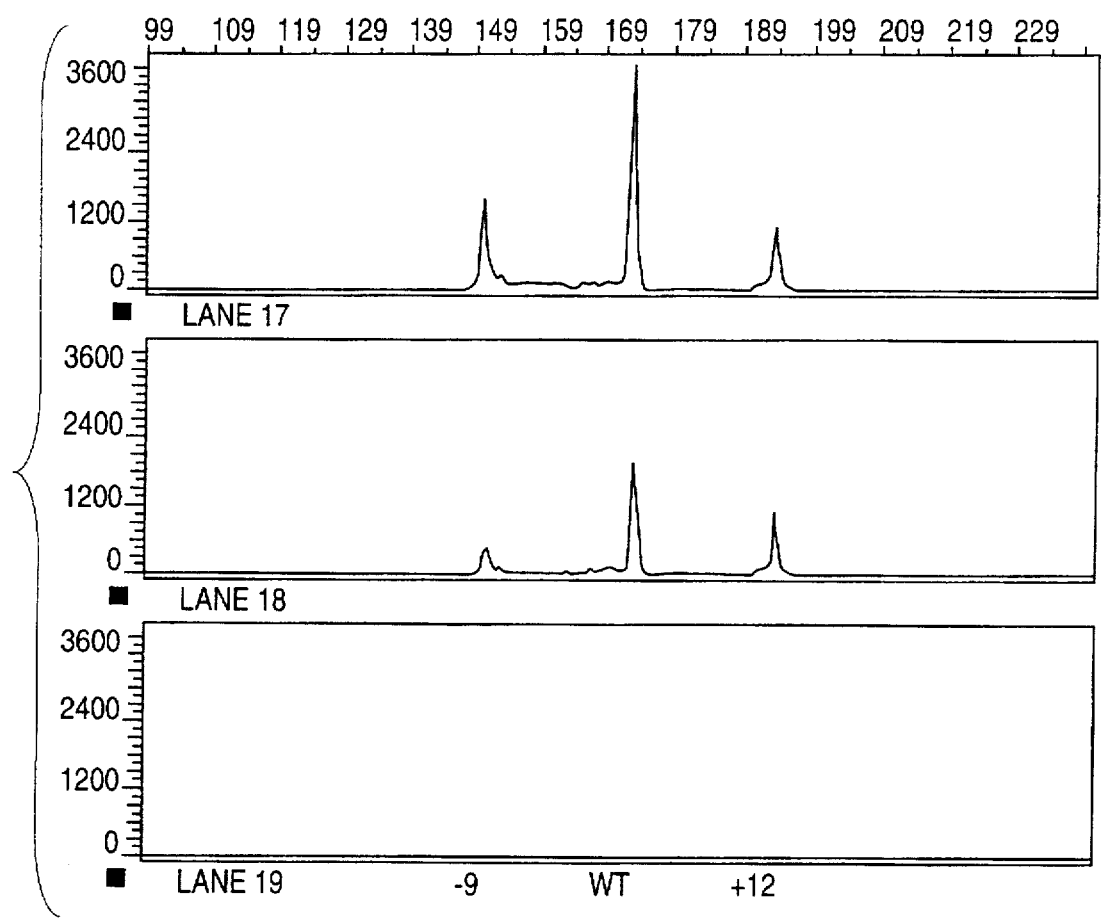
FIG. 4-E

METHOD OF QUANTITATING NUCLEIC ACID

The invention relates to a method of quantitating nucleic acids in a sample by applying nucleic acid amplification, wherein prior to the amplification step, a given amount of a known nucleic acid molecule is added to the sample as an internal standard, which standard nucleic acid molecule differs from the nucleic acid to be quantitated at least in one detectable characteristic.

At present, only very unreliable detection methods exist for diagnosing various viral diseases. Often it is not possible to diagnose a virus infection at an early stage of the disease, because the ELISA methods available are unable to detect the few virus proteins circulating in the blood. For a successful therapy it would, however, be of an enormous value to recognize infections as early as possible. Furthermore, it also holds for viral infections that the virus concentration in the blood fluctuates in the course of the illness or due to the influence of a therapy. In this context, the amount of virus particles may decrease so much that the conventional methods will prove not to be sensitive enough. In such cases, false negative results obtained by ELISA test will give a false impression of the course of the disease.

A further aspect in the detection of nucleic acids is the quality control of biotechnologically produced products. On the one hand, preparations of immunogenic virus proteins recovered from infectious viruses and utilized as vaccines must be checked for their content of contaminating viral nucleic acid. On the other hand, recombinant products produced with a viral expression system are checked with respect to contaminating nucleic acids which may be derived from the expression system. The limit values of contaminating nucleic acids allowed in this case have been fixed by the World Health Organization to be 100 pg per dose, and by the U.S. Food and Drug Administration to be 10 pg per dose.

Developments in PCR technology have made it possible to dramatically lower the detection limit for the detection of nucleic acids. However, especially with low nucleic acid concentrations, the reproducibility of the results still poses major problems. The reason for this is that, on the one hand, the technique has not yet been perfected, and, on the other hand, the copies of the nucleic acids to be detected often are only few. In the quantitative determination in this low range of concentration, errors in the analysis naturally will have particularly dramatic effects.

The skilled artisan knows very well that the efficiency of the PCR frequently may vary from reaction vessel to reaction vessel. This difference in efficiency may lead to differences in the results of up to $10^5$. The reproducibility of the quantitation data obtained with the known methods thus is still insufficient.

To improve the reproducibility of the PCRs, Gilliland (PNAS 87:2725 (1990)) has developed a competitive PCR method. For determining DNA amounts, a dilution series of an internal standard is used which is amplified simultaneously with the sample. The PCR is carried out up to saturation. This also allows for the detection of the PCR products by means of ethidium bromide staining. Subsequently, the PCR products are separated on a gel, the number of copies of the sample is compared with the number of copies of the standard dilution series, and thus the concentration of the sample is estimated. This concentration estimate will be exact if the concentration of the standard and of the sample have been amplified in a reaction vessel approximately in the ratio 1:1. This in turn implies that the determination of the DNA amount will be the more precise, the more standard dilutions have been used.

A method of quantitating RNA has been proposed by Wang et al. (PNAS 86 (1989), 9717). This PCR is stopped in the exponential phase. By amplification of differing standard concentrations, the authors provide a calibration curve. Since in the exponential reaction phase, the number of PCR products increases directly proportional to the number of PCR cycles and to the concentration of the RNA, this calibration curve is a straight line in which, finally, the concentrations of an amplified sample can be determined. A disadvantage of this method is that the final concentration of the PCR products is relatively low so that sensitive detection methods must be applied for the detection. Wang et al. use radioactively labelled nucleotides.

According to WO 93/23573, the concentration of viral RNA, in ranges of from $10^2$ to $10^8$ copies can be determined by competitive PCR. In multiple determinations of HIV-1, the reproducibility of this method is stated to have a variation coefficient of $0.26 \pm 0.15$. In this case, the determinations become the more precise, the more the concentration ratio of sample to standard approaches 1:1. It must be taken into consideration that, with this method, the standard RNA is added only after the sample has been pre-treated. However, when extracting the sample, up to 50% of the RNA may be lost. Thus, finally, the RNA amount originally contained in the sample is based on the standard which has been added after the extraction. In this manner, only the lowermost limit of a possible number of copies per sample is determined. The portions lost by extraction cannot be taken into consideration.

WO 94/20640 also describes a competitive RT PCR method of which it is stated that it enables the determination of 100 copies of the HIV genome in the plasma of HIV infected patients. Yet in ranges below 100 copies, determination of the concentration of the HIV genomes is effected merely by estimation. The standard deviation of determinations of copy numbers in the range of $10^4$ to $10^6$ copies thus is 22%, if a triple determination is made from the same plasma; in double determinations of the same RNA preparation, the standard deviation is 15% (WO 94/20640, page 22, lines 8–13). There, too, the extraction efficiency of the RNA extraction is not taken into consideration. The number of copies of the HIV RNA found are in the range of from $4.4 \times 10^3$ to $9.3 \times 10^6$. Only for one single patient, 100 copies are stated as an "extrapolated" value. Thus, the question arises whether this method is at all suitable for an exact determination of low numbers of copies (below $10^3$).

An improvement in the detection of small amounts of PCR products has been achieved by Porcher et al. (BioTechniques 13 (1992), 106) by the utilization of fluorescence-marked primers and quantitation of PCR products with an automatic laser fluorescence DNA sequencer.

The present invention aims at providing a method of quantitating nucleic acids, which allows for a very precise information which, above all, can be reproduced well, as regards the amount of nucleic acid present in a sample and simultaneously allows statements regarding the detection limit of the nucleic acid to be determined.

The method according to the invention and of the type initially mentioned is characterised in that, prior to nucleic acid amplification, known amounts of at least two known nucleic acid molecules, differing from each other and from the nucleic acid to be quantitated in at least one detectable characteristic, are added as an internal standard to the sample, the amounts of amplified sample and standard nucleic acids obtained are determined, and from the amounts obtained, the amount of nucleic acid to be quantitated which has originally been present in the sample is determined.

The method according to the invention surprisingly allows for a very exact quantitation of nucleic acids of all types, which, furthermore, can be reproduced well.

Nucleic acid amplification in principle refers to methods based on the techniques developed by Mullis et al. (U.S. Pat. Nos. 4,683,195 and 4,683,202), and others, e.g. the polymerase chain reaction (PCR), the reverse transcriptase-PCR (RT-PCR) or the ligase-CR (LCR).

The standard nucleic acid must differ from the nucleic acid to be quantitated in at least one detectable characteristic, yet it should be capable of being amplified by aid of the same primers. Standard nucleic acids which have a different size than the nucleic acid to be quantitated or which have a unique restriction cleavage site have proved to be convenient. When determining amounts of DNA, the standard nucleic acid preferably is a DNA, and when determining amounts of RNA, it preferably is an RNA. Preferred standards differ from the nucleic acid to be quantitated by their PCR products differing in 1% to 20% of their lengths and by differing by at least 3, maximally 50, nucleotides. A standard nucleic acid whose PCR product is longer than that of the nucleic acid to be determined is designated as "plus" ("+") standard, and a standard nucleic acid whose PCR product is smaller than that of the nucleic acid to be determined is designated as "minus"("−") standard. The precise sequence of the standard nucleic acid should, of course, be known.

In the method according to the invention, the standards are preferably used in different concentrations, one of the standards being added at a concentration of slightly above the detection limit.

The primers used in the amplification process preferably contain groups which increase the detection limit of the amplified nucleic acids, e.g. fluorescent or radioactive groups or chemical groups which can be detected with affine proteins and subsequent detection reactions (e.g. biotin-avidin, DIG labelling, etc.), primers having fluorescent groups being particularly preferred.

The determination of amounts of nucleic acids (by amount of nucleic acid, basically, the quantity of DNA or RNA is to be understood; an amount of nucleic acid may, e.g., be stated in the form of weight (mg, µg, ng, pg), or may be given as the number of copies of a certain nucleic acid molecule) following amplification may be effected in different ways, yet in most cases it has to comprise a step in which the amplified standard nucleic acid is separated from the amplified nucleic acid to be quantitated, and the separated amounts of nucleic acid are determined separately. Preferably, this separation step may consist of a gel electrophoresis or of a chromatographic method.

Detection methods which are automatic and which combine the separation and quantitation step have proved to be particularly suitable. A preferred embodiment of the method according to the invention consists in that the determination of the amounts of the amplified nucleic acid is effected by using a nucleic acid detection device, preferably a fluorescence-sensitive nucleic acid detection device. Examples of such nucleic acid detection devices are automatic DNA sequencers with laser-induced fluorescence measuring means (e.g. Gene Scanner®373A of Applied Biosystems), HPLC or capillary electrophoresis system devices. With these devices it is possible to separate nucleic acid molecules which differ in length merely by one bp.

A particular advantage of the Gene Scanner® is that it is possible to differentiate between different fluorescent dyes in one single lane. This allows for the simultaneous processing of a plurality of samples on one gel, since all lanes available on the gel may be used for samples. Furthermore, it is possible to analyse a plurality of PCR products, labelled with different fluorescent dyes, in one single lane (multiplex-PCR). When simultaneously detecting two different nucleic acids, e.g., in one sample, furthermore expenditures and costs are nearly cut in half. When using the method according to the invention in a routine operation, this is of particular advantage, e.g., when a blood sample is to be tested for HIV and HCV. In contrast thereto, the automatic laser fluorescence DNA sequencer used by Porcher et al. for analysing PCR products can analyse only one fluorescent dye (and thus only one DNA) per lane.

A preferred embodiment of the method according to the invention thus relates to a method in which several amounts of amplified sample and standard nucleic acids obtained are determined by means of the multiplex analysis in the same sample.

In a preferred embodiment of the method according to the invention, the amplification step is stopped already in the exponential phase.

Thereby the ratio of the number of copies of the amplified standard is directly proportional to the number of copies of the sequence to be quantitated. Furthermore, by co-amplification of a single standard, the number of copies of the nucleic acid to be determined can be determined. In this respect the method according to the invention is by far superior to the frequently used method of Gilliland et al., since only one measurement with at least two different standard molecules need be carried out per sample, whereas the method according to Gilliland is the more precise, the more standards are used in different dilutions in different samples.

A particularly preferred field of application of the method according to the invention consists in the quantitation of nucleic acids from microorganisms, preferably nucleic acids from HIV, Parvo virus, herpes virus, HAV, HBV, HCV, Baculo virus, Adeno virus, influenza virus, vaccinia virus, borrelia species, salmonella species or yeast. These microorganisms are of interest both as pathogens and because of their use in the production of vaccines and of recombinant proteins.

In particular, the method according to the invention is applied in the quantitation of viral nucleic acids which may remain as contaminations in biotechnologically produced products. Preferably, these biotechnological products may be immunogenic virus proteins or virus parts which are recovered from infectious viruses by biotechnological methods; or they may be recombinantly produced products produced with a viral expression system and which may contain contaminations of the viral nucleic acid of the expression system.

Preferably, viral nucleic acids are quantitated in a biological sample, in particular in human plasmas and their derivatives, according to the method of the invention. With the present method, the course of an infection or the monitoring of treatment by vaccination or therapy, e.g., can be monitored in a better and more precise manner.

Therein it is of particular importance that by the method according to the invention, pathogenic viruses can be determined at a concentration which is below the infectious dose of these viruses by at least one power of ten.

To obtain as precise a value as possible for the nucleic acid quantitation in a sample, which value will not be influenced by manipulations of the sample to be examined, according to a preferred embodiment of the method of the invention, the standards are directly added to the sample, preferably prior to the extraction step, whereupon thus subsequently the nucleic acids of the sample and the nucleic acids of the standard are subjected to the same sample preparation (co-extraction). This allows for a quantitation result which not only has an increased and unfalsified reproducibility, but furthermore is independent of sample preparation manipulations.

A further aspect of the present invention thus relates to a method of determining the detection limit of certain nucleic acids, in which at least one standard nucleic acid is used at a concentration of slightly above the detection limit.

Preferably, the amount of nucleic acid is calculated as the number of copies according to the following formula:

$$N_{sample}=A_{sample}/A_{standard} \times N_{standard} \times F \times D,$$

wherein $A_{sample}$ is the peak area of the amplified nucleic acid of the sample, $A_{standard}$ is the peak area of the amplified internal standard, $N_{standard}$ is the number of used copies of the internal standard, F is the ratio of the unit volume to the extracted volume, and D is the dilution factor (if the sample has been diluted prior to extraction).

For the particular field of application of the method according to the invention, in which contaminating viral nucleic acids are to be quantitated, the amount of nucleic acid is given in pg/ml so as to meet the requirements of WHO and FDA. According to the invention, the following formula is used therefor:

$$m_{sample}=A_s/A_{st} \times N_{st} \times F1 \times D \times F2,$$

wherein $A_s$=the peak area of the PCR product of the sample, $A_{st}$=the peak area of the PCR product of the standard, $N_{st}$=the number of copies of the standard plasmid, F1=the ratio of the unit volume to the extracted volume, D =the dilution factor of the sample (if required), and F2=the mass of a viral molecule in pg (molecular weight of the viral DNA/Avogadro constant).

Since, according to the method of the invention, at least two standards of differing concentrations are used, according to the above-described calculation at least two values for the concentration of the sample are obtained, from which finally the mean value is calculated. In routine operation, as a rule two set-ups of each sample with at least two standards are analysed, whereby finally a mean value from four values can be established for the concentration of the sample.

The method according to the invention is characterised by a particularly high reproducibility. The standard deviation obtained in multiple determinations is 15% at the most, yet generally below 10%, even if the number of copies is in the low range of concentration of $10^2$. These extremely low standard deviations are particurlarly surprising since in multiple determinations, the respective samples together with the standard are also separately prepared each time, which means that also errors in handling and efficiency differences in the extraction of the sample and in the PCR as such are included in these standard deviations.

The standard deviations of 0.26±0.15 or of 22% or 15%, respectively, described in WO 93/23573 and WO 94/20640 were obtained in that the sample, after preparation thereof, is divided into various parts and these parts are used to determine the reproducibility. Thus efficiency differences which may be due to sample extraction or RT-PCR, respectively, are not included in the determination of the standard deviation, thus necessarily resulting in a better, even though falsified, reproducibility.

The efficiency of the PCR is, e.g., influenced by the type of the nucleic acid molecule to be amplified. If the method according to the invention is used to determine RNA viruses, one will be confronted with the generally known problem that the reverse transcription is incomplete and only a few percent of the RNA present will actually be transcribed. Furthermore, it has been shown that the efficiency of amplification for the "+" and "−" standards, respectively, may differ in individual determinations, yet will be equal in its mean. This may result in fluctuations in the concentrations to be determined.

According to a preferred embodiment of the invention, thus, different amounts of the at least two standard nucleic acids are added to the sample prior to amplification so as to increase the information obtained.

To exclude further inaccuracies in the determination of the concentration of the sample, thus two aliquots are determined per sample in the routine process, at least two standards being co-amplified therewith in each case. In this manner, four measured values are obtained per sample, from which it is then possible to calculate a mean value. In the examples, the precision and reproducibility of the method is clearly demonstrated. It is also demonstrated that the method yields reproducible results over a wide range of concentrations.

According to a preferred embodiment of the method according to the invention, two standard nucleic acids are used which have a length different from that of the nucleic acid to be quantitated, preferably one standard nucleic acid sequence which is shorter and one standard nucleic acid sequence which is longer than the nucleic acid to be quantitated. A particularly preferred difference in length ranges between 1% and 20%.

For the method of the invention it has proved to be advantageous to add the nucleic acid of the internal standard to the PCR in the linearised form. Thus, further differences in the efficiency of the reaction which are due to different forms of the nucleic acid to be amplified are compensated.

Important criteria in the quantitation of nucleic acids are—as stated before—the sensitivity and the reproducibility. With the method according to the invention, nucleic acid amounts in the range of from 1 to 500 copies can be determined substantially more precisely and more reproducible than with the methods described in the prior art. Thus, however, the reproducibility limit of the method is not reached by any means.

The spectrum of use of the method according to the invention includes, e.g., the qualitative and quantitative analysis of biological samples in respect of nucleic acids, in particular of blood and blood derivatives and of biotechnological products. A further exemplary field of application is the diagnosis and/or monitoring of the course of an infection as well as the monitoring of treatment by vaccination and therapy.

An important aspect of the invention thus concerns biological products, in particular biotechnological products which have a content of nucleic acids below the permissible limits of 10 or 100 pg, respectively, per dose, preferably below the range of from 1 to 100 copies per sample, measured by the method according to the invention, which thus can be deemed as substantially free from nucleic acids.

The preferred products include viral and bacterial proteins, such as gp160, recombinant blood factors, plasma proteins as well as vaccines, in particular against herpes, influenza, TBE, Parvo or hepatitis viruses and monoclonal antibodies.

According to a further aspect, the present invention also relates to the use of the method according to the invention for the detection of nucleic acids in biological samples.

Furthermore, the quality control, particularly in the field of vaccines or biotechnologically produced proteins, is faced with background problems. Thus, when determining contaminating nucleic acid (chromosomal DNA, RNA, viral DNA and RNA) in cell cultures from primates, also contaminations due to handling during production or during preparation of the products can be covered by the method of the invention, if the primers used are specific. However, if the production of recombinant proteins is effected in cell cultures of non-primates, such as, e.g. CHO (Chinese Hamster Ovaries), BHK (Baby Hamster Kidney cells) or CEC (Chicken Embryo Cells), the detection limit is far lower with the method according to the invention, since the problem of contaminations caused by handling the sample is eliminated. The use of the quantitation method of the invention is particularly preferred for nucleic acids derived from CHO, vero (monkey cell line), BHK, SK Hep1 (human liver cell line), hybridoma or CEC cells, since these cell cultures are the most usually used in the production of vaccines or of biotechnologically produced proteins.

Selection of the primer pairs is, of course, also an important factor for obtaining a good quantitation. Thus, the present invention, according to another aspect thereof, relates to primers which are used in the present method, namely HAV+2058:ACTGCCATTGGGAAGCTTATTGTG HAV 2058-2081 Seq.ID 3, HAV−2172:CATCCATAGCATGATAAAGAGGAGC HAV 2196-2172 Seq.ID 4, (numbering according to Cohen at al. (J. Virol.61 (1987) 50–59))

HCV32EXT: CTGTGAGGAACTACTGTCTTACGCAG HCV 45-70 Seq.ID 5,

HCVPT4: CGGTTCCGCAGACCACTATG HCV 158-139 Seq.ID 6, (numbering according to Han et al. (PNAS 88 (1991) 1711–1715))

HBV+1780B:CATTGATCCTTATAAAGAATTTGGAGC HBV 1780-1806 Seq.ID 7 and

HBV−1960B:CCAGCAGAGAATTGCTTGCCTGAG HBV 1983-1960 Seq.ID 8

(numbering according to Fujiyama et al. (Nucleic Acids Res. 11 (1983) 4601–4610))

oprl-r: AAA ATA GGA TCA TGA TGG C Vaccinia 84625-84644 Seq. ID 9, oprl-f: ATA TTA GAT GGT GCC ACC GT Vaccinia 84761-84743 Seq. ID 10

(numbering according to Goebel et al. Virology 179: 247–266, 1990), gD1/B: AACTACCCCGATCATCAG HSV 138364-138381 Seq.ID 11, gD2R/B: AGGCCCACTATGACGACA HSV 138477-138456 Seq. ID 12

(McGeoch D. J., et al., EMBL GenBank ID HE1CG)

and plasmids for the production of the standards, namely pgag1 (consisting of the known pBS/SK−plasmid and an insert between Pst I and Apa I sites of the multiple cloning site, which insert contains the base pairs (bp) 1417 to 2008 of the HIV-1 sequence of Ratner et al. (Nature 313 (1985), 277–284), pgag−15 (derived from pgag1 with a deletion of 15 bp starting from bp 1593 of the HIV-1 sequence of Ratner et al.), pgag+12 (derived from pgag1 by making an insertion of 12 nucleotides at the bp1593 site), pHAV−wt (consisting of the known pCRII plasmid and an insert at the multiple cloning site of the pCRII plasmid, which insert contains the bp 2020 to 2226 of the cDNA sequence of Cohen et al.), pHAV−10bp (derived from pHAV−wt with a deletion of 10 bp starting from bp 2100 of the HAV sequence of Cohen et al.)

pHAV+9bp (derived from pHAV−wt, by making an insertion of 9 nucleotides at the bp2100 site), pHCV−wt (consisting of the known pBS/SK−plasmid and an insert at the EcoRV site of this plasmid, which insert contains the bp27 to 313 of the cDNA sequence of Han et al.)

pHCV−7bp (derived from pHCV−wt with a deletion of 7bp starting from bp126 of the HCV sequence of Han et al.)

pHCV+8bp (derived from pHCV−wt by making an insertion of 8 nucleotides at the bp126 site), pHBV−wt (consisting of the known pCRII plasmid and an insert, which insert contains the bp 1763 to 2032 of the HBV genome according to Fujiyama et al.), pHBV−9bp (derived from pHBV−wt with a deletion of 9bp starting from bp 1868 of the HBV sequence of Fujiyama et al.), pHBV+12bp (derived from pHBV−wt, by making an insertion of 12 nucleotides at the bp1868 site)

pVV−wt (derived from the known pTZ19R plasmid of Pharmacia with an insert between the two PvuII sites of that plasmid, which insert contains the bp83855 to 84761 of the thymidin-kinase gene of the vaccinia virus (according to Goebel et al., 1990)), pVV−21 (derived from pVV−wt with a deletion of 21 nucleotides (bp84718 to 84738)), pVV+24 (derived from pVV−wt with an insertion of 24 bp at the 84713 site), pHerp (derived from the known pCRII plasmid (of In Vitrogen) and an insert, which insert contains the bp 138364 to 138784 of the HSV genome according to McGeoch et al., EMBL GenBank DE 1 CG1), pHerp−9 (derived from p−Herp with a deletion of 9 nucleotides (bp 138388 to 138396)) and pHerp+10 (derived from p−Herp with an insertion of 10 bp at bp 138407).

According to a further aspect, the present invention also relates to a kit for quantitating nucleic acids in a sample comprising at least two known nucleic acids as internal standards differing from each other and from the nucleic acids to be quantitated in at least one detectable characteristic, fluorescence labelled primers binding to the standard nucleic acid and the nucleic acid to be quantitated, positive controls comprising known amounts of a nucleic acid of interest, a negative control comprising human plasma free of viral nucleic acid of interest and a manual.

Preferred embodiments of the kit according to the present invention are as follows:

1. A kit for quantitating HIV-RNA in a sample comprising at least two internal standards comprising in vitro transcribed RNA derived from plasmids pgag–15 and pgag+12 fluorescence labelled primers SK38 and SK39 a positive control comprising known amounts of HIV-1 particles a negative control comprising human plasma free of viral nucleic acids and a manual.

2. A kit for quantitating HCV-RNA in a sample comprising at least two internal standards comprising in vitro transcribed RNA derived from plasmids pHCV–7 and pHCV+8 fluorescence labelled primers HCV32Ext and HCVPT4 positive controls comprising known amounts of HCV particles a negative control comprising human plasma free of viral nucleic acids and a manual.

3. A kit for quantitating HAV-RNA in a sample comprising at least two internal standards comprising in vitro transcribed RNA derived from plasmids pHAV–10 and pHAV+9 fluorescence labelled primers HAV+2058 and HAV–2172 positive controls comprising known amounts of HAV particles a negative control comprising human plasma free of viral nucleic acids and a manual.

4. A kit for quantitating HBV-DNA in a sample comprising at least two internal standards comprising plasmids pHBV–9 and pHBV+12 fluorescence labelled primers HBV+1780B and HBV–1960B positive controls comprising known amounts of HBV particles a negative control comprising human plasma free of viral nucleic acids and a manual.

5. A kit for quantitating HSV-DNA in a sample comprising as internal standards plasmids pHerp–9 and pHerp+10 fluorescence labelled primers gDR/B and gDR2R/B positive controls comprising known amounts of HSV particles a negative control comprising human plasma free of viral nucleic acids and a manual.

The invention will be explained in more detail by way of the following examples and the associated drawing figures to which, however, it shall not be limited. In particular, the examples illustrate that the method according to the invention is excellently suited for a routine, quick, yet precise and reproducible quantitation of nucleic acids in the most varying samples.

There are illustrated in

FIG. 1 the cloning of pgag–15 and pgag+12;

FIG. 2A–2F containing graphs A–F are the results of quantitating HIV with RT-PCR;

FIG. 3-A and 3-B are the results of quantitating HAV with RT-PCR

FIG. 4A through 4-E are the results of quantitating HBV; and

EXAMPLES

1. General working instructions 1.1. Principle of the method

Nucleic acids of different origin are amplified by means of PCR with the use of primers containing fluorescent groups (Saiki et al., Science 239 (1985) 487–491). Analysis and quantitation of the amplified PCR products obtained were carried out with the aid of an automatic DNA sequencer with a laser-induced fluorescence measuring device (DNA Sequencer 373A with Gene Scan® software from Applied Biosystems). This instrument is capable of separating according to size the fluorescence-labelled PCR products by means of a gel electrophoresis in a polyacryl amide gel under denaturing conditions and to determine their amounts quantitatively. The number of copies of certain sequences in the sample is determined on the basis of the obtained intensities of the PCR products of nucleic acids to be quantitated and at least two internal standards.

1.2.1. Extraction of DNA of viral particles

500 µl of the sample are centrifuged in an ultracentrifuge at 70000 rpm for 20 min. The pellet is dissolved in 500 µl of 10 mM TRIS/HCl pH 8.0 and 10 µl of proteinase K (Boehringer Mannheim, 20 mg/ml), as well as 10 µl of 20% SDS. A certain amount of standard nucleic acid and 1 µg herring sperm DNA is added and the sample is incubated for 1 hour at 56° C. The sample is successively extracted with phenol and chloroform, and 10 µl of glycogen (Boehringer Mannheim, 20 mg/ml) are added. Subsequently, it is precipitated with ethanol, centrifuged, the pellet is washed and finally dissolved again in water.

1.2.2. Extraction of proviral DNA $5 \times 10^5$ cells are lysed in 100 µl lysis buffer (1×PCR buffer of Boehringer, 0.5 mg/ml Proteinase K, 0.45% Tween) for 5 h at 56° C. Aliquots thereof are used for the PCR.

1.2.3. Extraction of viral residual DNA

500 µl of the sample are dissolved in 5 µl of 10 mM TRIS/HCl pH 8.0, and 10 µl of proteinase K (Boehringer Mannheim, 20 mg/ml). After incubating over night at 37° C. or for 4 h at 56° C., a certain amount of standard nucleic acid is added, the sample is successively extracted with phenol and chloroform, and 10 µl of glycogen (Boehringer Mannheim, 20 mg/ml) are added. Subsequently, it is precipitated with ethanol, centrifuged, the pellet is washed, and finally dissolved again in water.

1.2.4. Extraction of RNA 1 ml of plasma or of plasma diluted with PBS, respectively, is centrifuged at 70000 rpm for 20 min. The supernatant is removed by suction. The pellet is taken up in 1 ml of guanidium isothiocyanate solution (RNAzol® of Biotec), and 5 µl 1 mg/ml t-RNA from yeast and a certain amount, e.g. 20 µl, of standard RNA are added. A predetermined number, e.g. 400 and 1200, copies of the minus- and plus-RNA standards are added and vortexed. The solution is heated for 10 min at 70° C., then 1/10 volume of chloroform is added and incubated on ice for 10 min. Thereupon it is centrifuged in a table-top centrifuge for 5 min, the supernatant is transferred into new vials. 500 µl of isopropanol are added and adjusted to −80° C. for 15 min. Subsequently, it is centrifuged for 10 min, washed twice with 70% ethanol, and the pellet is taken up in 50 µl of water. 5 µl are used for the RT-PCR.

1.3.1. PCR for the detection of DNA

The PCR set-up contains, in a known manner, one aliquot of the extracted nucleic acid, PCR buffer (Boehringer Mannheim), $MgCl_2$, dNTPs, primer, Taq-DNA-polymerase (Boehringer Mannheim, 5.0 U/µl) and water. The PCR is carried out according to the instructions of the producers of buffer and enzyme, and according to the common working instructions (Mullis et al., Methods in Enzymology 155 (1987), 335), respectively, in a PCR apparatus (GeneAmp PCR System 9600 of Perkin-Elmer).

1.3.2. RT-PCR for the detection of RNA

The RT-PCR set-up contains, in a known manner, one aliquot of the extracted nucleic acid, RT buffer of Perkin-Elmer, $MgCl_2$, dNTPs, the RT primer and rT.th.polymerase (Perkin-Elmer, 2.5 U/µl) and water. The RT is carried out according to the instructions of the producers of buffer and enzyme and according to the common working instructions (Mullis et al., Methods in Enzymology 155 (1987), 335), respectively, in a PCR apparatus (GeneAmp PCR System 9600 of Perkin-Elmer).

For the PCR, furthermore $MgCl_2$, a chelate buffer and the second primer are added. Then the PCR is carried out according to the above-described instructions.

1.4. Analysis of the products

For determining and quantitating the PCR products, 0.5 to 1.0 µl of the PCR solution are taken and analysed in a 373A instrument of Applied Biosystems according to the instructions of the producer.

1.5. Array of controls in (RT)-PCR

In addition to stringent internal controls, an array of positive and negative controls assures the PCR results. In the different controls, the standards are added at different steps of the analytical procedure (List 1).

List 1. Array of Controls in (RT)-PCR
Type Comment

Negative Controls k1** Reagent blank control. Addition of water to RT-mix and PCR-mix. The handling is done in the area where the stock solutions are stored. The sample is kept on ice until PCR. This control provides information concerning contamination in the reagents.

k3** Contamination control. Addition of water instead of extract to the RT-mix. Analysis is carried out as for the other samples. This control provides information concerning contamination caused by the handling procedure in the area where the RT-PCR is performed.

k4* Contamination control. Analysis of an extract made from a negative control plasma or PBS. This control detects false positive results due to the extraction procedure. Internal standards are not added.

Positive Controls k5* Internal standard/reagent control. Direct additon of the internal standards into the RT-PCR/PCR reaction without prior extraction. This control tests the integrity of the internal standards and the functionality of the reagents.

k6*** Verifier control. Analysis of a defined amount of verifier derived from wild-type standard plasmids by in vitro transcription. This control tests the extraction procedure and the amount of the internal standards.

k7* Virus particle control. Analysis of an aliquot containing a defined amount of viral particles diluted to an appropriate concentration in negative plasma or PBS. This control tests the overall performance of the assay applied.

* the controls k4, k5 and k7 are performed in each extraction series;
** the controls k1 and k3 are performed as soon as false positive wild-type signals appear;
*** k6 is performed only when new batches of internal standards are prepared; control k2 has been omitted since the introduction of the one-enzyme one-tube procedure described here.

2. Example 1

Quantitation of HIV by reverse transkriptase-PCR (RT-PCR)

In this quantitation primers are used which bind in the cDNA sequences of HIV-1 and which yield a product of 115 bp by means of RT-PCR of wild-type RNA, namely SK38: ATAATCCACCTATCCCAGTAGGAGAAAT
HIV-1 1551-1578 Seq.ID 1
SK39: TTTGGTCCTTGTCTTATGTCCAGAATGC
HIV-1 1665-1638 Seq.ID 2

(Numbering according to Ratner et al.). The primers were produced by using the phosphoamidite chemistry on a DNA synthesizer (Applied Biosystems 394 DNA Synthesizer)

The standard plasmids pgag−15 and pgag+12 are derived from the plasmid pgag1 which consists of the known pBS/SK⁻plasmid (of Stratagene) and an insert in the multiple cloning site of this plasmid, which insert contains the bp 1417 to 2008 of the HIV-1 from Ratner et al.

In pgag−15, the bp 1593 to 1607 were deleted, in pgag+12 an insert of 12 bp was inserted at site 1593 (cf. FIG. 1). The plasmids were purified (QUIAGEN method), the concentration was determined by spectroscopic measurement at 260 nm, and diluted in a 10 mM TRIS/HCl pH 8/0.1 mM EDTA buffer (Sambrook et al., Molecular Cloning, Second Edition, Cold Spring Harbor Lab Press, Cold Spring Harbor (1989)).

After linearising with Asp718, the in vitro transcription with T3 polymerase according to Sambrook et al. yields a 644 b "+" transcript and a 617 b "−" transcript which are extracted with a guanidino isothiocyanate solution and quantitated by spectrophotometrical measurement at 260 nm.

These RNA preparations serve as standard for the RT-PCR.

The length of the RT-PCR products of the standard and of the wild-type DNA thus are 127 (pgag+12), 100 (pgag−15) and 115 bp (wt).

FIG. 2, graphs A and B illustrate the results of a control experiment. Two samples of 100 copies of wt-RNA each, produced from the plasmid pgag1, are extracted according to the method described above, amplified by co-amplification with "−" and "+" standard and analysed by "gene scanning". In both lanes, the PCR products of "−" "wt" and "+" standard can be recognized. The results of the quantitative evaluation of these chromatograms are given in Table 1, lines 1 and 2.

The columns "N−added" and "N+added" indicate the number of copies added of "−" and "+" standard. "Dilution"

indicates the dilution factor by which the sample has been diluted, "Volume" indicates the worked-up volume. "Sample" indicates the sample code, "Comment" contains further information regarding the sample. "GS#, Lane" indicates the analyse run and the number of the lane in that run, respectively. "A–", "Awt" and "A+" indicate the peak areas, i.e. the intensity of the PCR products of "–", "wt" and "+". "N–base" and "N+base" contains the result, given in copies per ml sample, calculated according to the formula set out above. The column "Final Result" give the mean values of these values.

114 and 106 copies, respectively, were measured for the samples, wherein to both samples 100 copies were added. A good correlation is found between the theoretical value (i.e. copies wt added) and measured value (i.e. copies wt determined). The deviations are +14 and +6%, respectively. From this it can be concluded that an unknown amount of wt-RNA can be determined with this method.

For a further control experiment, a negative plasma was admixed with a preparation of HIVIIIB, whose infectiousness had previously been determined in vitro. The virus concentration in the plasma was 200 TCID$_{50}$ per ml. 0.5 ml each of a 1:10 and of a 1:40 dilution, respectively, were analysed as described above. The results are given in FIG. 2, graphs C and D as well as in lines 3 and 4 of Table 1. For both samples, there resulted a copy number in the undiluted plasma of 33187 and 25895, respectively, per ml. The deviation from the mean value is 12%. This experiment shows that the number of HIV copies measured in a sample is indepedent of the amount used in the assay.

FIG. 2, graphs E and F as well as lines 5 and 6 of Table 1 show the results of the determination of an unknown sample. In two independent determinations, 5612 and 5828 copies, respectively, were measured. The deviation is 2%. From this it can be concluded that the above described method is suited for a sensitive and precise determination of HIV.

When measuring various dilutions of the same sample, the higher deviation can be attributed to the additional error on account of dilution.

(Numbering according to Cohen et al. (J. Virol. 61 (1987) 50–59)). The primers were produced by using the phosphoamidite chemistry on a DNA synthesizer (Applied Biosystems 394 DNA Synthesizer).

The standard plasmids pHAV–10 and pHAV+9 are derived from the plasmid pHAV-wt which consists of the known pCRII plasmid (of InVitrogen) and an insert in the multiple cloning site of that plasmid, which insert contains the bp 2020 to 2226 of the HAV from Cohen et al.

In pHAV–10, the pb 2100 to 2109 were deleted, in pHAV+9 an insert of 9 bp was inserted at the site 2100. The plasmids were purified (QUIAGEN method), the concentration was determined by spectroscopical measurement at 260 nm, and diluted in a 10 mM TRIS/HCl pH 8/0.1 mM EDTA buffer (Sambrook et al., Molecular Cloning, Second Edition, Cold Spring Harbor Lab Press, Cold Spring Harbor (1989)).

After linearising with AlwNI, the in vitro transcription with T7-polymerase according to Sambrook et al. results in a 1140 b "+" transcript, a 1121 b "–" transcript and a 1131 b "wt" transcript, which are extracted with a guanidino isothiocyanate solution and quantitated by spectrophotometric measurements at 260 nm.

These RNA preparations serve as standard for the RT-PCR.

The length of the RT-PCR products of standard and wild-type DNA are 148 (pHAV+9), 129 (pHAV–10) and 139 bp (wt).

Two plasmas (PL1 and PL2) as well as two albumin solutions (albumin and human albumin) were assayed for HAV by means of the methods described. Table 2 shows the evaluation of the measurements with the nucleic acid detection device with the aid of a computer program (MS Excel®). Columns 1 and 2 indicate the amounts of minus standard and plus standard used. Columns 3 and 4 indicate dilultion and volume used. In column 5 the sample is indicated, column 6 gives the virus in respect of which the assay is carried out. The copy numbers of the samples are calculated both by way of the minus standard (N–base; column 7) and by way of the plus standard (N+base; column 8); the mean value of both determinations is the measured

TABLE 1

| | N– added | N+ added | Dilution | Volume | Sample | Comment | N– Base | N+ Base | Final result | GS #, Lane | A– | A wt | A+ |
|---|---|---|---|---|---|---|---|---|---|---|---|---|---|
| 1 | 500 | 1500 | 1 | 1 | k6.931020.31 | 100 cop. wt add. | 109 | 120 | 114 | 126, 20 | 10303 | 2254 | 28092 |
| 2 | 500 | 1500 | 1 | 1 | k6.931020.41 | 100 cop. wt add. | 76 | 136 | 106 | 126, 21 | 22353 | 3441 | 37739 |
| 3 | 250 | 750 | 10 | 0.5 | HIV 940328.11 | control plasma | 21079 | 45296 | 33187 | 194, 01 | 11199 | 47214 | 15635 |
| 4 | 250 | 750 | 40 | 0.5 | HIV 940328.31 | control plasma | 22821 | 28969 | 25895 | 194, 03 | 10400 | 11867 | 24578 |
| 5 | 500 | 1500 | 1 | 0.25 | 477.21 | sample | 5349 | 5875 | 5612 | 147, 01 | 12181 | 32580 | 33270 |
| 6 | 500 | 1500 | 1 | 0.25 | 477.31 | sample | 7460 | 4197 | 5828 | 149, 10 | 10981 | 40964 | 58561 |

3. Example 2

Quantitation of HAV by RT-PCR

In this quantitation, primers were used which bind in the cDNA sequences of HAV and give a 139 bp product by RT-PCR of wild-type RNA, namely HAV+2058:ACTGCCATTGGGAAGCTTATTGTG HAV 2058-2081 Seq.ID 3 and HAV–2172:CATCCATAGCATGATAAAGAGGAGC HAV 2196-2172 Seq.ID 4 result. Column 9 remains blank. Column 10 gives the number of the sample run. Columns 11, 12 and 13 indicate the areas of the detected peaks.

FIGS. 3-A and 3-B illustrate the graphic evaluation of the HAV assay, wherein in the various lanes the intensities of the fluorescence signals of the PCR products (and by-products) are illustrated. The products can be identified by means of their defined size (in bp). The standards have lengths of 148 and 129 bp, the wild-type has a length of 139.

TABLE 2

| 900 | 300 | 1 | 0.25 | PL 1 | HAV | 918 | 677 | — | 314, 17 | 22213 | 5666 | 10040 |
|---|---|---|---|---|---|---|---|---|---|---|---|---|
| 900 | 300 | 1 | 0.25 | Albumin 1 | HAV | −1 | −1 | — | 318, 18 | 19805 | −1 | 2814 |
| 900 | 300 | 1 | 0.25 | Human Albumin 1 | HAV | −1 | −1 | — | 314, 19 | 13995 | −1 | 7308 |
| 900 | 300 | 1 | 0.25 | PL 2 | HAV | −1 | −1 | — | 314, 20 | 29283 | −1 | 4278 |
| 1 | 2 | 3 | 4 | 5 | 6 | 7 | 8 | 9 | 10 | 11 | 12 | 13 |

The results of these assays showed that Plasma 1 was positive (798 copies/ml), whereas the other samples were below the detection limit. The "detection limit peak" (the plus-standard in a copy number of 300 copies/ml of extracted material) is clearly visible in all measurements.

4. Example 3

Quantitation of HCV by RT-PCR

In this quantitation, primers are used which bind in the cDNA sequences of the HCV and which give a product having a size of 114 bp by means of RT-PCR of wild-type RNA, namely HCV32EXT: CTGTGAGGAACTACTGTCTTACGCAG HCV 45-70 Seq.ID 5 and HCVPT4: CGGTTCCGCAGACCACTATG HCV 158-139 Seq.ID 6 (Numbering according to Han et al. (PNAS 88 (1991) 1711–1715)). The primers were produced by using the phosphoamidite chemistry on a DNA synthesizer (Applied Biosystems 394 DNA Synthesizer).

The standard plasmids pHCV−7 and pHCV+8 are derived from the plasmid pHCV−wt, which consists of the known pBS/SK⁻plasmid (of Stratagene) and an insert in the multiple cloning site of that plasmid, which insert contains the bp 27 to 313 of the HCV of Han et al.

In pHCV−7 the bp 126 to 135 were deleted, in pHCV+8 an insert of 8 bp was inserted at site 126. The plasmids were purified (QUIAGEN method), the concentration was determined by spectroscopic measurement at 260 nm, it was cleaved with XmnI and diluted in a 10 mM TRIS/HCl pH 8/0.1 mM EDTA buffer (Sambrook et al., Molecular Cloning, Second Edition, Cold Spring Harbor Lab Press, Cold Spring Harbor (1989)).

In vitro transcription with T3 polymerase according to Sambrook et al. yields a 1385 b "+" transcript, a 1370 b "−" transcript and a 1377 b "wt" transcript, which are extracted with a guanidino isothiocyanate solution and quantitated by spectrophotometric measurements at 260 nm.

These RNA preparations serve as standard for the RT-PCR.

The lengths of the RT-PCR products of standard and wild-type DNA thus are 122 (pHCV+8), 107 (pHCV−7) and 114 bp (wt).

Two samples with 200 and 2000 copies, respectively, of wt-RNA, produced from the plasmid pHCV−wt were extracted according to the above-described method, amplified by co-amplification with "−" and "+" standard and analysed by "gene scanning". In both lanes, the PCR-products of "−", "wt" and "+" standards are recognizable. The results of the quantitative evaluation of these chromatograms are indicated in lines 1 and 2 of Table 3. This table is set up analogous to Example 1.

1972 and 193 copies, respectively, were measured for the samples, wherein 2000 and 200 copies, respectively, had been added to the samples. It is found that there is a good correlation between the theoretical value (i.e. copies wt added) and the measured value (i.e. copies wt determined). The deviations are −1 and −3%, respectively. From this it can be concluded that an unknown amount of wt-RNA can be determined by this method.

A pool of HCV positive plasma from various-patients was used for a further control experiment. 0.5 ml each of a 1:125 and of a 1:625 dilution, respectively, were analysed as described above. The results are given in lines 3 and 4 of Table 3. For both samples, there results a number of copies of 1215157 and 898327, respectively, per ml in the undiluted pool. The deviation from the mean value is 15%. This experiment shows that the measured number of copies of HCV in a sample is independent of the amount used in the assay. Furthermore, this example shows that the reproducibility of the method according to the invention is not only given in the range of a low number of copies, but also in the range of a large number of copies.

Lines 5 and 6 of Table 3 illustrate the results of the determination of an unknown sample. In two independent determinations, 3277 and 3676 copies, respectively, were measured. The deviation is 5%. From this it can be concluded that the above-described method is suitable for the sensitive and precise determination of HCV.

The higher deviation in measurements of various dilutions of the same sample can be attributed to the additional error caused by dilution.

TABLE 3

| | N−added | N+added | Dilution | Volume | Sample | Comment | N−Base | N+Base | Final result | GS #, Lane | A− | A wt | A+ |
|---|---|---|---|---|---|---|---|---|---|---|---|---|---|
| 1 | 400 | 1200 | 1 | 1 | HCV 940314 21 | 2000 Copies wt | 2915 | 1030 | 1972 | 181, 02 | 1053 | 7676 | 8942 |
| 2 | 400 | 1200 | 1 | 1 | HCV 940314 31 | 200 Copies wt | 234 | 152 | 193 | 181, 03 | 1100 | 644 | 5052 |
| 3 | 400 | 1200 | 125 | 0.5 | HCV 940328 41 | plasma | 1864107 | 566208 | 1215157 | 192, 12 | 560 | 10439 | 5581 |
| 4 | 400 | 1200 | 625 | 0.5 | HCV 940328.51 | plasma | 637312 | 1159343 | 595327 | 102, 13 | 4264 | 5435 | 7032 |
| 5 | 400 | 1200 | 1 | 1 | sample 1A | no | 4563 | 1992 | 3277 | 204, 03 | 492 | 5613 | 3380 |
| 6 | 400 | 1200 | 1 | 1 | sample 1B | no | 3690 | 3662 | 3676 | 204, 04 | 614 | 5665 | 1856 |

5. Example 4
Quantitation of HIV-proviral DNA

In this quantitation primers are used which bind in the cDNA sequences of HIV-1 and yield a product having a size of 115 bp by PCR of HIV-proviral DNA, namely SK38: ATAATCCACCTATCCCAGTAGGAGAAAT
HIV-1 1551-1578 Seq.ID 1

SK39: TTTGGTCCTTGTCTTATGTCCAGAATGC
HIV-1 1665-1638 Seq.ID 2

(Numbering according to Ratner et al.). The primers were produced by using the phosphoamidite chemistry on a DNA synthesizer (Applied Biosystems 394 DNA Synthesizer).

The standard plasmids pgag–15 and pgag+12 are derived from the plasmid pgag1 which consists of the known pBS/SK⁻plasmid (of Stratagene) and an insert in the multiple cloning site of that plasmid, which insert contains the bp 1417 to 2008 of the HIV-1 of Ratner et al.

In pgag–15, the bp 1593-1607 were deleted, in pgag+12 an insert of 12 bp was inserted at site 1593 (cf. FIG. 1). The plasmids were purified (QUIAGEN method), the concentration was determined by spectroscopic measurement at 260 nm, it was cleaved with EcoRI and diluted in a 10 mM TRIS/HCl pH 8/0.1 mM EDTA buffer (Sambrook et al., Molecular Cloning, Second Edition, Cold Spring Harbor Lab press, Cold Spring Harbor (1989)).

These DNA preparations serve as a standard for the PCR.

The lengths of the PCR products of standard and wild-type DNA thus are 127 (pgag+12), 100 (pgag–15) and 115 pb (wt).

The results of a quantitation series are given in Table 4. An encoded control series of positive and negative samples containing HIV proviral DNA in different numbers of copies was determined with the method of the invention. Table 4 shows that all the negative controls were quantitated as negative and all the positive samples were quantitated as positive in the correct size range. Particularly noteworthy is the precise measurement in the lower range of copies, cf. CD-13 and CD-26. These samples contained nominally 2 copies/$10^5$ cells and were quantitated with 3 copies each. This illustrates the precision and the extreme sensitivity of the method according to the invention.

TABLE 4

| SAMPLE | COPY NUMBER Actual | Found | SAMPLE | COPY NUMBER Actual | Found |
|---|---|---|---|---|---|
| CD-1 | 0 | 0 | CD-16 | 0 | 0 |
| CD-2 | 50 | 68 | CD-17 | 0 | 0 |
| CD-3 | 0 | 0 | CD-18 | 0 | 0 |
| CD-4 | 0 | 0 | CD-19 | 2 | 5 |
| CD-5 | 10 | 24 | CD-20 | 20 | 16 |
| CD-6 | 0 | 0 | CD-21 | 0 | 0 |
| CD-7 | 0 | 0 | CD-22 | 0 | 0 |
| CD-8 | 10 | 16 | CD-23 | 10 | 18 |
| CD-9 | 20 | 49 | CD-24 | 0 | 0 |
| CD-10 | 0 | 0 | CD-25 | 0 | 0 |
| CD-11 | 5 | 6 | CD-26 | 2 | 3 |
| CD-12 | 5 | 5 | CD-27 | 50 | 71 |
| CD-13 | 2 | 3 | CD-28 | 0 | 0 |
| CD-14 | 0 | 0 | CD-29 | 5 | 5 |
| CD-15 | 0 | 0 | CD-30 | 20 | 25 |

6. Example 5
Quantitation of HBV

In this quantitation primers are used which bind in the genome of the HBV and yield a product of 182 bp by PCR of wild-type DNA, namely HBV+
1780B:CATTGATCCTTATAAAGAATTTGGAGC
HBV 1780-1806 Seq.ID 7 and HBV–1960B:CCAGCAGAGAATTGCTTGCCTGAG
HBV 1983-1960 Seq.ID 8

(Numbering according to Fujiyama et al.). The primers were produced by using the phosphoamidite chemistry on a DNA synthesizer (Applied Biosystems 394 DNA Synthesizer).

The standard plasmids pHBV–9 and pHBV+12 are derived from the plasmid pHBV–wt which consists of the known pCRII plasmid (of In Vitrogene) and an insert in the multiple cloning site of that plasmid, which insert contains the bp 1763 to 1868 of the HBV of Fujiyama et al.

In pHBV–9 the bp 1868 to 1876 were deleted, in pHBV+12 an insert of 12 bp was inserted at site 1868. The plasmids were purified (QUIAGEN method), the concentration was determined by spectroscopic measurement at 260 nm, it was cleaved once with a restriction enzyme and diluted in a 10 mM TRIS/HCl pH 8/0.1 mM EDTA buffer (Sambrook et al., Molecular Cloning, Second Edition, Cold Spring Harbor Lab Press, Cold Spring Harbor (1989)).

These DNA preparations serve as the standard for the PCR.

The lengths of the PCR products of standard and wildtype DNA thus are 194 (pHBV+12), 173 (pHBV–9) and 182 bp (wt).

The results of a quantitation series are given in Table 5 and graphically depicted in FIGS. 4-A through 4-E. The amplification reaction was carried out each starting from 150 copies pHBV–9 and 50 copies of HBV+12 and different amounts of pHBV–wt (400, 200, 100, 50 and 0 copies). Each set-up was measured four-fold.

TABLE 5

| LANE | CODE | A – 9 | A – WT | A + 12 copies – 9 | copies + 12 | COPIES 1 | COPIES 2 | AVERAGE | RESULTS | A – 12/A – 15 |
|---|---|---|---|---|---|---|---|---|---|---|
| lane 1 | 400 Kp. | 11405 | 13730 | 4461 | 150 | 50 | 301.2 | 307.8 | 334.5 | 2.6 |
| lane 2 | 400 Kp. | 33124 | 31652 | 9668 | 150 | 50 | 286.7 | 327.4 | 307.0 | 3.4 |
| lane 3 | 200 Kp. | 18598 | 15623 | 6960 | 150 | 50 | 250.4 | 223.0 | 236.7 | 2.7 |
| lane 4 | 200 Kp. | 30630 | 19323 | 8380 | 150 | 50 | 189.3 | 230.8 | 209.9 | 3.7 |
| lane 5 | 100 Kp. | 24400 | 5270 | 6731 | 150 | 50 | 64.8 | 78.3 | 71.5 | 3.6 |
| lane 6 | 100 Kp. | 18766 | 7532 | 5581 | 150 | 50 | 102.4 | 135.0 | 127.7 | 3.4 |
| lane 7 | 50 Kp. | 34103 | 4244 | 6193 | 150 | 50 | 37.3 | 51.6 | 44.6 | 5.5 |
| lane 8 | 50 Kp. | 20818 | 3591 | 8570 | 150 | 50 | 37.4 | 41.9 | 39.6 | 2.4 |
| lane 9 | K5 | 33264 | –1 | 10199 | 150 | 50 | 0.0 | 0.0 | 0.0 | |
| lane 10 | K5 | 15217 | –1 | 5303 | 150 | 50 | 0.0 | 0.0 | 0.0 | |
| lane 11 | K3 | –1 | –1 | –1 | | | | | | |
| lane 12 | K3 | –1 | –1 | –1 | | | | | | |

The results show that the DNA content determined can be reproduced very well.

7. Example 6
Quantitation of the DNA of herpes simplex virus (HSV)

In this quantitation primers were used which bind in the genome of HSV and give a product of 114 bp by PCR of wild-type DNA, namely gDR1/B: AAC TAC CCC GAT CAT CAG Seq.ID 11
gDR2R/B: AGG CCC ACT TAG ACG ACA Seq.ID 12

The standard plasmid pHerp–9 is derived from the plasmid pHerp which consists of the known pCRII plasmid (of In Vitrogen) and an insert of bp 128364 to 138784 of the HSV genome (McGeoch D. J. et al., EMBL GenBank ID HE1CG1).

9 bp were deleted in pHerp–9. The plasmids were purified, the concentration was determined by spectroscopic measurement at 260 nm, it was linearised with a restriction enzyme and diluted in a TE buffer (10 mM Tris/HCl, 1 mM EDTA, pH 8).

This DNA preparation serves as a standard for the PCR. The lengths of the PCR products of standard and wild-type thus are 105 (pHerp–9) and 114 bp (pHerp).

The results of a quantitation are given in Table 6. Five samples as well as 1.66 pg pHerp wild-type DNA were analysed in the presence of 40000 (column 1) copies of standard pHerp–9 by means of the method described. The factor F2 of the described formula for calculating the herpes DNA amount in this case is 1/6000. Columns 2 and 3 state the dilution factor as well as the used volume of the sample. Column 4 gives the name of the sample. Column 5 contains additional information on the samples (if necessary). In column 6, the calculated amount of HSV-DNA in pg/ml is stated. The mean value of the double determination is given in column 7. Columns 8 and 9 give the areas of the detected peaks of standard plasmid (column 8) and of wild-type (column 9).

For samples 14, 17 and JA10, double determinations of herpes-DNA are made which contain a deviation from the mean value of from 0% to 4.3%. This slight standard deviation may be dramatically improved if the pHerp+10 standard is also co-determined in the determinations.

TABLE 6

| N– added | Dilution | Vol. | Sample | Comment | pg/ml | Final result | A– | A wt |
|---|---|---|---|---|---|---|---|---|
| 40000 | 1 | 0.1 | 0000.00 | Herpes | 1333 | — | 100 | 10000 |
| 40000 | 1 | 0.5 | sample 14.11 | — | 3.1 | 3 | 7872 | 1840 |
| 40000 | 1 | 0.5 | sample 14.12 | — | 2.9 | — | 8171 | 1774 |
| 40000 | 1 | 0.5 | sample 16.11 | — | 5.5 | 5.75 | 11105 | 4626 |
| 40000 | 1 | 0.5 | sample 16.12 | — | 6 | — | 7266 | 3311 |
| 40000 | 1 | 0.5 | sample 17.11 | — | 1.7 | 1.7 | 12402 | 1570 |
| 40000 | 1 | 0.5 | sample 17.12 | — | 1.7 | — | 9118 | 1181 |
| 40000 | 1 | 0.5 | YES 10.11 | — | 1.6 | 1.65 | 10713 | 1315 |
| 40000 | 1 | 0.5 | YES 10.12 | — | 1.7 | — | 9200 | 1148 |
| 40000 | 1 | 0.5 | H2O | — | 0 | 0 | 7843 | –1 |
| 40000 | 1 | 0.5 | H2O | — | 0 | — | 4077 | –1 |
| 40000 | 1 | 0.5 | PCR | — | 0 | 0 | –1 | –1 |
| 40000 | 1 | 0.5 | PCR | — | 0 | — | –1 | –1 |
| 10000 | 1 | 1 | 1.66 pg wt 1.2 | — | 1.8 | — | 3863 | 4362 |
| 1 | 2 | 3 | 4 | 5 | 6 | 7 | 8 | 9 |

8. Example 7
Quantitation of vaccinia-DNA

In this quantitation primers were used which bind in the genome of the vaccinia virus and yield, by PCR of wild-type DNA, a product of 136 bp, namely oprl-r AAA ATA GGA TCA TGA TGG C bp 84626-84644 oprl-f ATA TTA GAT GGT GCC ACC GT bp 84761-84743 (Numbering according to Goebel et al., Virology 179: 247–266, 1990). The primers were produced on a DNA synthesizer (Applied Biosystems 394 DNA Synthesizer).

The standard plasmid pVV–21 is derived from the plasmid pVV–wt which consists of the know n pTZ19R plasmid (Pharmacia) and an insert between the two PvuII restriction cleavage sites of that plasmid. This insert contains the bp 83855 to 84761 of the thymidine kinase gene region of the vaccinia virus (cf. Goebel et al., 1990).

21 bp (from bp 84718 to 84738) were deleted in pVV-21.

The plasmids were purified, the concentration was determined by spectroscopic measurement at 260 nm, it was linearised with a restriction enzyme and diluted in a TE buffer (10 mM Tris/HCl, 1 mM EDTA, pH 8).

This DNA preparation serves as the standard for the PCR. The lengths of the PCR products of standard and wild-type thus are 115 (pVV-21) and 136 (pVVwt).

The results of a quantitation are given in Table 7. Samples, water and 10 pg of vaccinia DNA were analysed in the presence of 10000 copies of standard plasma (column 1) by means of the method described. The value of the factor F2 of the described formula for the calculation of the vaccinia DNA in pg/ml is 1/5000 in this instance.

Columns 2 and 3 indicate the dilution factor as well as the used volume of the sample. In column 5 more information on the sample may be given (if necessary). Column 4 gives the name of the sample. In column 6, the calculated amount of vaccinia DNA in pg/ml is given. Column 7 gives the number of the gene scanner run, in which the PCR products have been analysed. Columns 8 and 9 state the areas of the detected peaks of standard plasmid (column 8) and of wild-type (column 9).

In sample 311494, 1.64 pg and 1.77 pg, respectively, of vaccinia DNA, are measured, the deviation from the mean value being 3.8%. In sample 310494, 7.0 pg and 7.2 pg, respectively, of vaccinia DNA, are measured, the deviation from the mean value being 1.4%. This slight standard deviation may be improved dramatically if also the pVV+24 standard is co-determined in the determinations.

TABLE 7

| N– added | Dilution | Volume | Sample | Comment | pg/ml | GS #, Lane | A– | A wt |
|---|---|---|---|---|---|---|---|---|
| 45000 | 1 | 0.5 | 0000.00 | no | 1800 | 261, 00 | 100 | 10000 |
| 40000 | 1 | 1 | 10 pg | no | 10.6 | 259, 06 | 35836 | 47165 |
| 40000 | 5 | 0.5 | 310494 | no | 7 | 216, 09 | 55109 | 4820 |
| 40000 | 5 | 0.5 | 310494 | no | 7.2 | 216, 01 | 37886 | 3375 |
| 40000 | 5 | 0.5 | 311494 | no | 1.64 | 246,18 | 49362 | 1013 |
| 40000 | 5 | 0.5 | 311494 | no | 1.77 | 246, 20 | 48816 | 1079 |
| 40000 | 1 | 0.5 | H2O | no | –1 | 246, 21 | 41041 | –1 |
| 40000 | 1 | 1 | PCR | no | 0 | 246, 27 | –1 | –1 |
| 1 | 2 | 3 | 4 | 5 | 6 | 7 | 8 | 9 |

What we claim is:

1. In a method of quantitating nucleic acids in a sample using nucleic acid amplification and comprising the steps of providing a sample containing said nucleic acid to be quantitated, subjecting said sample to at least one sample preparation step, and adding a given amount of a known nucleic acid molecule as an internal standard before carrying out said nucleic acid amplification, the improvement comprising:

adding to said sample, prior to said at least one sample preparation step, known amounts of at least two known nucleic acid molecules as said internal standard, wherein said at least two known nucleic acid molecules differ in length from each other and from said nucleic acid to be quantitated and wherein said at least two known nucleic acid molecules and said nucleic acid to be quantitated are amplified by the same primers, carrying out said at least one sample preparation step and said nucleic acid amplification, determining, in a first determination, the amounts of the amplified molecules of said nucleic acid to be quantitated in said sample and of said standard nucleic acids obtained, and determining from said obtained amounts in a second determination, the amount of said nucleic acid to be quantitated originally contained in the sample.

2. A method as set forth in claim 1, further comprising using primers in said nucleic acid amplification, said primers containing groups selected from the group consisting of fluorescent groups, radioactive groups and chemical groups, said chemical groups contained in said primers being detectable by affinity proteins and subsequent detection reactions.

3. A method as set forth in claim 1, further comprising using primers in said nucleic acid amplification, said primers containing fluorescent groups.

4. A method as set forth in claim 1, wherein said amplification of said nucleic acids is stopped already in the exponential phase.

5. A method as set forth in claim 1, wherein said first determination is effected by using a nucleic acid detection device selected from the group consisting of an HPLC device and a capillary electrophoresis device.

6. A method as set forth in claim 1, wherein said first determination is effected by using a fluorescence-sensitive nucleic acid detection device.

7. A method as set forth in claim 1, wherein said nucleic acids to be quantitated are nucleic acids of microorganisms.

8. A method as set forth in claim 7, wherein said microorganisms are selected from the group consisting of HIV, Parvo virus, herpes virus, HAV, HBV, HCV, Baculo virus, Adeno virus, vaccinia virus, borrelias, salmonella and yeast.

9. A method as set forth in claim 7, wherein said nucleic acids to be quantitated are viral nucleic acids and said sample is a biological sample.

10. A method as set forth in claim 9, wherein said biological sample is selected from the group consisting of blood, blood derivatives and biotechnological products.

11. A method as set forth in claim 1, wherein different amounts of said standard nucleic acids are added to said sample prior to said nucleic acid amplification.

12. A method as set forth in claim 1, wherein one of said standard nucleic acids has a shorter nucleic acid sequence than the nucleic acid to be quantitated and another one of said standard nucleic acids has a longer nucleic acid sequence than the nucleic acid to be quantitated.

13. A method as set forth in claim 1, wherein said first determination is a multiplex analysis destined to determine several obtained amounts of amplified sample and standard nucleic acids in the same sample.

14. A method of determining the detection limit of certain nucleic acids using a method of quantitating nucleic acids in a sample by means of nucleic acid amplification comprising:

providing a sample containing said nucleic acid to be quantitated, adding known amounts of at least two known nucleic acid molecules as an internal standard to said sample before carrying out said nucleic acid amplification, wherein said at least two standard nucleic acid molecules differ in length from each other and from said nucleic acid to be quantitated and wherein said at least two standard nucleic acid molecules and said nucleic acid to be quantitated are amplified by the same primers, carrying out said nucleic acid amplification, determining, in a first determination, the amounts of the amplified sample and standard nucleic acids obtained, and determining from said obtained amounts, in a second determination, the amount of said nucleic acid to be quantitated originally contained in said sample, wherein at least one of said standard nucleic acid molecules is added at a concentration exceeding the concentration of nucleic acid at the detection limit.

15. A method as set forth in claim 1 to be used for detecting nucleic acids in biological samples.

16. A kit for quantitating nucleic acids in a sample comprising at least two known nucleic acids as internal standards differing in length from each other and from the nucleic acids to be quantitated, wherein said at least two known nucleic acids and said nucleic acid to be quantitated are amplified by the same primers, fluorescence labelled primers binding to the standard nucleic acid and the nucleic acid to be quantitated, a positive controls comprising a known amount of a nucleic acid of interest, and a a negative control comprising human plasma free of viral nucleic acid of interest.

17. A kit according to claim 16 for quantitating HIV-RNA in a sample comprising at least two internal standards comprising in vitro transcribed RNA derived from plasmids pgag–15 and pgag+12 fluorescence labelled primers SK38 and SK39 a positive control comprising known amounts of HIV-1 particles a negative control comprising human plasma free of viral nucleic acids.

18. A kit according to claim 16 for quantitating HCV-RNA in a sample comprising at least two internal standards comprising in vitro transcribed RNA derived from plasmids pHCV–7 and pHCV+8 fluorescence labelled primers HCV32Ext and HCVPT4 positive controls comprising known amounts of HCV particles a negative control comprising human plasma free of viral nucleic acids.

19. A kit according to claim 16 for quantitating HAV-RNA in a sample comprising at least two internal standards comprising in vitro transcribed RNA derived from plasmids pHAV–10 and pHAV+9 fluorescence labelled primers HAV+2058 and HAV–2172 positive controls comprising known amounts of HAV particles a negative control comprising human plasma free of viral nucleic acids.

20. A kit according to claim 16 for quantitating HBV-DNA in a sample comprising at least two internal standards comprising plasmids pHBV–9 and pHBV+12 fluorescence labelled primers HBV+1780B and HBV–1960B positive controls comprising known amounts of HBV particles a negative control comprising human plasma free of viral nucleic acids.

21. A kit according to claim 16 for quantitating HSV-DNA in a sample comprising as internal standards plasmids pHerp–9 and pHerp+10 fluorescence labelled primers gDR/B and gDR2R/B positive controls comprising known amounts of HSV particles a negative control comprising human plasma free of viral nucleic acids.

22. A method as set forth in claim 3, wherein the primers are selected from the group consisting of SEQ ID NOS: 1, 2, 3, 4, 5, 6, 7, 8, 9, 10, 11 and 12.

23. A method according to claim 1, wherein the standard nucleic acid molecules are selected from the group consisting of pgag1, pgag–15, pgag+12, pHAV–wt, pHAV–10 bp, pHAV+9 bp, pHCV–wt, pHCV–7 bp, pHCV+8 bp, pHBV–wt, pHBV–9 bp, pHBV+12 bp, pVV–21, pVV+24 and pHERP+10.

24. A method of quantitating nucleic acid molecules in a sample, comprising:

contacting a sample containing a nucleic acid test molecule to be quantitated with at least two known nucleic acid control molecules, wherein the nucleic acid control molecules differ in length from each other and from the nucleic acid test molecule to be quantitated, and wherein the nucleic acid test molecule and the at least two known nucleic acid control molecules are amplified by the same primers;

amplifying all nucleic acid molecules;

determining the amount of amplified nucleic acid test molecule and amplified nucleic acid control molecules, and then determining the amount of nucleic acid test molecule originally in the sample based upon the amounts of amplified nucleic acids obtained.

25. A method according to claim 24, wherein the amplifying step employs nucleic acid primers.

26. A method according to claim 24, wherein the primers are selected from the group consisting of SEQ ID NOS: 1, 2, 3, 4, 5, 6, 7, 8, 9, 10, 11 and 12.

27. A method according to claim 24, wherein the known nucleic acid control molecules are selected from the group consisting of pgag1, pgag–15, pgag+12, pHAV–wt, pHAV–10 bp, pHAV+9 bp, pHCV–wt, pHCV–7 bp, pHCV+8 bp, pHBV–wt, pHBV–9 bp, pHBV+12 bp, pVV–21, pVV+24 and pHERP+10.

28. A method according to claim 1, wherein said sample preparation step is a nucleic acid extraction step.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ATAATCCACC TATCCCAGTA GGAGAAAT                        2 8

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTTGGTCCTT GTCTTATGTC CAGAATGC                        2 8

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear -continued (xi) SEQUENCE DESCRIPTION: SEQ ID NO:3:

ACTGCCATTG GGAAGCTTAT TGTG  24

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

CATCCATAGC ATGATAAAGA GGAGC  25

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

CTGTGAGGAA CTACTGTCTT ACGCAG  26

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

CGGTTCCGCA GACCACTATG  20

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:7:

CATTGATCCT TATAAAGAAT TTGGAGC  27

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

CCAGCAGAGA ATTGCTTGCC TGAG  24

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:9:

```
AAAATAGGAT CATGATGGC                                                                19
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
ATATTAGATG GTGCCACCGT                                                               20
```

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AACTACCCCG ATCATCAG                                                                 18
```

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AGGCCCACTA TGACGACA                                                                 18
```